United States Patent
Han et al.

(10) Patent No.: US 7,834,007 B2
(45) Date of Patent: Nov. 16, 2010

(54) CGRP ANTAGONISTS

(75) Inventors: Xiaojun Han, Cheshire, CT (US); Prasad V. Chaturvedula, Cheshire, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1120 days.

(21) Appl. No.: 11/508,568

(22) Filed: Aug. 23, 2006

(65) Prior Publication Data

US 2007/0049577 A1    Mar. 1, 2007

Related U.S. Application Data

(60) Provisional application No. 60/711,294, filed on Aug. 25, 2005.

(51) Int. Cl.
*A61K 31/54* (2006.01)
*A61K 31/535* (2006.01)
*A61K 31/50* (2006.01)
*A61K 31/435* (2006.01)
*A61K 31/41* (2006.01)
*A01N 43/66* (2006.01)
*A01N 43/58* (2006.01)
*A01N 43/40* (2006.01)
*A01N 43/64* (2006.01)
*C07D 417/00* (2006.01)
*C07D 413/00* (2006.01)
*C07D 403/00* (2006.01)
*C07D 241/02* (2006.01)
*C07D 401/00* (2006.01)

(52) U.S. Cl. ............ 514/222.2; 544/60; 544/120; 544/295; 544/357; 544/360; 544/372; 514/228.8; 514/241; 514/247; 514/277; 514/359

(58) Field of Classification Search .......... None
See application file for complete search history.

(56) References Cited

U.S. PATENT DOCUMENTS

| | | | |
|---|---|---|---|
| 5,939,425 A * | 8/1999 | Caruso | 514/289 |
| 6,313,097 B1 | 11/2001 | Eberlein et al. | |
| 6,344,449 B1 | 2/2002 | Rudolf et al. | |
| 6,521,609 B1 | 2/2003 | Doods et al. | |
| 6,552,043 B1 | 4/2003 | Patchett et al. | |
| 2001/0036946 A1 | 11/2001 | Rudolf et al. | |
| 2003/0139417 A1 | 7/2003 | Eberlein et al. | |
| 2003/0181462 A1 | 9/2003 | Doods et al. | |
| 2003/0191068 A1 | 10/2003 | Trunk et al. | |
| 2003/0212057 A1 | 11/2003 | Rudolf et al. | |
| 2003/0236282 A1 | 12/2003 | Hurnaus et al. | |
| 2004/0002495 A1 | 1/2004 | Sher et al. | |
| 2004/0014679 A1 | 1/2004 | Trunk et al. | |
| 2004/0063735 A1 | 4/2004 | Chaturvedula et al. | |
| 2004/0076587 A1 | 4/2004 | Kruss et al. | |
| 2004/0132716 A1 | 7/2004 | Rudolf et al. | |
| 2004/0192729 A1 | 9/2004 | Rudolf et al. | |
| 2004/0204397 A1 | 10/2004 | Chaturvedula et al. | |
| 2004/0214819 A1 | 10/2004 | Rudolf et al. | |
| 2004/0229861 A1 | 11/2004 | Burgey et al. | |
| 2004/0248816 A1 | 12/2004 | Doods et al. | |
| 2005/0032783 A1 | 2/2005 | Doods et al. | |
| 2005/0065094 A1 | 3/2005 | Davidai | |
| 2005/0153959 A1 | 7/2005 | Luo et al. | |
| 2005/0215546 A1 | 9/2005 | Hurnaus et al. | |
| 2005/0215576 A1 | 9/2005 | Degnan et al. | |
| 2005/0227968 A1 | 10/2005 | Lustenberger et al. | |
| 2005/0233980 A1 | 10/2005 | Doods et al. | |
| 2005/0234054 A1 | 10/2005 | Mueller et al. | |
| 2005/0234067 A1 | 10/2005 | Mueller et al. | |
| 2005/0250763 A1 | 11/2005 | Mueller et al. | |
| 2005/0256098 A1 | 11/2005 | Burgey et al. | |
| 2005/0256099 A1 | 11/2005 | Mueller et al. | |
| 2005/0272955 A1 | 12/2005 | Zimmer et al. | |
| 2006/0094707 A1 | 5/2006 | Chaturvedula et al. | |
| 2006/0122250 A1 | 6/2006 | Chaturvedula et al. | |
| 2006/0229447 A1 | 10/2006 | Chaturvedula et al. | |

FOREIGN PATENT DOCUMENTS

| | | |
|---|---|---|
| CA | 2 387 613 | 5/2001 |
| CA | 2 503 455 | 4/2005 |

(Continued)

OTHER PUBLICATIONS

Dorwald F. A. Side Reactions in Organic Synthesis, 2005, Wiley: VCH, Weinheim pg. IX of Preface.*

(Continued)

*Primary Examiner*—James O Wilson
*Assistant Examiner*—Jeffrey H Murray
(74) *Attorney, Agent, or Firm*—James Epperson

(57) ABSTRACT

The present invention encompasses compounds of Formula I

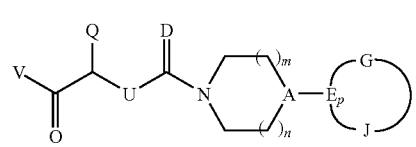

(I)

which are antagonists of calcitonin gene-related peptide receptors ("CGRP-receptor"), pharmaceutical compositions comprising them, methods for identifying them, methods of treatment using them and their use in therapy for treatment of neurogenic vasodilation, neurogenic inflammation, migraine and other headaches, thermal injury, circulatory shock, flushing associated with menopause, airway inflammatory diseases, such as asthma and chronic obstructive pulmonary disease (COPD), and other conditions the treatment of which can be effected by the antagonism of CGRP-receptors.

10 Claims, No Drawings

FOREIGN PATENT DOCUMENTS

| | | |
|---|---|---|
| EP | 1 227 090 A1 | 7/2002 |
| WO | WO 97/09046 | 3/1997 |
| WO | WO 98/09630 | 3/1998 |
| WO | WO 98/11128 | 3/1998 |
| WO | WO 9844922 * | 10/1998 |
| WO | WO 98/56779 | 12/1998 |
| WO | WO 99/52875 | 10/1999 |
| WO | WO 00/18764 | 4/2000 |
| WO | WO 00/55154 | 9/2000 |
| WO | WO 01/32648 | 3/2001 |
| WO | WO 01/25228 | 4/2001 |
| WO | WO 01/32649 | 5/2001 |
| WO | WO 01/49676 | 7/2001 |
| WO | WO 02/10140 | 2/2002 |
| WO | WO 03/027252 | 4/2003 |
| WO | WO 03/070753 | 8/2003 |
| WO | WO 03/076432 | 9/2003 |
| WO | WO 03/104236 | 12/2003 |
| WO | WO2004/002960 A1 | 1/2004 |
| WO | WO 2004/037810 | 5/2004 |
| WO | WO 2004/082602 A2 | 9/2004 |
| WO | WO 2004/082605 A2 | 9/2004 |
| WO | WO 2004/082678 A1 | 9/2004 |
| WO | WO 2004/083187 A1 | 9/2004 |
| WO | WO 2004/087649 A2 | 10/2004 |
| WO | WO 2004/091514 A2 | 10/2004 |
| WO | WO 2004/092166 A2 | 10/2004 |
| WO | WO 2004/092168 A1 | 10/2004 |
| WO | WO 2005/000807 | 1/2005 |
| WO | WO 2005/009962 | 2/2005 |
| WO | WO 2005/013894 | 2/2005 |
| WO | WO 2005/056550 | 5/2005 |
| WO | WO 2005/065779 | 7/2005 |
| WO | WO 2005/072308 | 8/2005 |
| WO | WO2005/084672 | 9/2005 |
| WO | WO 2005/092880 | 10/2005 |
| WO | WO 2005/095383 | 10/2005 |
| WO | WO/2005/100343 | 10/2005 |
| WO | WO/2005/100352 | 10/2005 |
| WO | WO/2005/100360 | 10/2005 |
| WO | WO 2005/102322 | 11/2005 |
| WO | WO 2005/103037 | 11/2005 |
| WO | WO/2005/121078 | 12/2005 |
| WO | WO 2006/052378 | 5/2006 |
| WO | WO 2006/060678 | 6/2006 |

OTHER PUBLICATIONS

Vippagunta et. al. Advanced Drug Delivery Reviews 48 (2001) 3-26.*

Amara, S.G., et al., Science, 1982, 298:240-244, "Alternate RNA processing in calcitonin gene expression generates mRNAs encoding different polypeptide products", Nature, 1982, 15: 240-244.

Ashina, M., et al., "Evidence for increased plasma levels of calcitonin gene-related peptide in migraine outside of attacks", Pain, 2000, 86(1-2):133-138.

Brain, S.D., et al., "CGRP receptors: a headache to study, but will antagonists prove therapeutic in migraine?", TiPS, 2002, 23(2): 51-53.

Carlström, A.-S. and Frejd, T., "Palladium-Catalyzed Bis-coupling of Dihaloaromatics with 2-Amidoacrylates", J. Org. Chem., 1991, 56: 1289-1293.

Carlström, A.-S. And Frejd, T., Palladium-Catalyzed Synthesis of Didehydroamino Acid Derivatives, Synthesis, 1989, 6, 414-418.

Chu, D.Q., et al., "The calcitonin gene-related peptide (CGRP) antagonist CGRP8-37 blocks vasodilatation in inflamed rat skin: involvement of adrenomedullin in addition to CGRP," Neuroscience Letters, 2001, 310:169-172.

De Vries, P., et al., "Pharmacological aspects of experimental headache models in relation to acute antimigraine therapy," European Journal of Pharmacology,1999, 375: 61-74.

Doods, H., et al., "Pharmacological profile of BIBN4096BS, the first selective small molecule CGRP antagonist," British Journal of Pharmacology, 2000, 129: 420-423.

Dygos, J.H., "A Convenient Asymmetric Synthesis of the Unnatural Amino Acid 2,6-Dimethyl-L-tyrosine", Synthesis, 1992, 741-743.

Edvinsson, L., "Calcitonin Gene-Related Peptide (CGRP) and the Pathophysiology of Headache", CNS Drugs, 2001, 15(10):745-753.

Escott, K.J., et al., "Effect of a calcitonin gene-related peptide antagonist (CGRP8-37) on skin vasodilatation and oedema induced by stimulation of the rat saphenous nerve", British Journal of Pharmacology, 1993, 110, 772-776.

Evans, B.N. et al., "CGRP-RCP, a Novel Protein Required for Signal Transduction at Calcitonin Gene-related Peptide and Adrenomedullin Receptors", J. Biol. Chem., 2000, 275(4): 31438-31443.

Gallai, V., et al. "Vasoactive peptide levels in the plasma of young migraine patients with and without aura assessed both interictally and ictally", Cephalalgia, 1995;15: 384-390.

Goadsby, P.J., et al., "Vasoactive peptide release in the extracerebral circulation of humans during migraine headache", Annals of Neurology, 1990, 28(2):183-187.

Grant, A.D., "Evidence of a role for NK1 and CGRP receptors in mediating neurogenic vasodilatation in the mouse ear", British Journal of Pharmacology, 2002, 135: 356-362.

Hall, J.M. and Brain, S.D., "Interaction of amylin with calcitonin gene-related peptide receptors in the microvasculature of the hamster cheek pouch in vivo," British Journal of Pharmacology, 1999, 126: 280-284.

Hall, J.M., et al., "Interaction of human adrenomedullin 13-52 with calcitonin gene-related peptide receptors in the microvasculature of the rat and hamster," British Journal of Pharmacology, 1995, 114: 592-597.

Juaneda, C. et al. "The molecular pharmacology of CGRP and related peptide receptor subtypes", TiPS, 2000, 21: 432-438.

Lassen, L.H. et al. "CGRP may play a causative role in migraine", Cephalalgia, 2002, 22(1): 54-61.

Mallee, J.J., et al. "Receptor Activity-modifying Protein 1 Determines the Species Selectivity of Non-peptide CGRP Receptor Antagonist", J. Biol. Chem., 2002, 277(16): 14294-14298.

McLatchie, L.M. et al., "RAMPs regulate the transport and ligand specificity of the calcitonin-receptor-like receptor", Nature, 1998, 393: 333-339.

Olesen, J. et al., "Calcitonin Gene-Related Peptide Receptor Antagonist BIBN 4096 BS for the Acute Treatment of Migraine", New England J. of Medicine, 2004, 350 (11): 1104-1110.

Pasternak, A., et al., "Potent, orally bioavailable somatostatin agonists: good absorption achieved by urea backbone cyclization", Bioorganic & Medicinal Chemistry Letters, Oxford GB, vol. 9, No. 3, Feb. 8, 1999, p. 491-496.

Poyner, D.R. et al., "Pharmacological characterization of a receptor for calcitonin gene-related peptide on rat, L6 myocytes", British Journal of Pharmacology, 1992, 105: 441-447.

Rosenfeld, M.G., et al., "Production of a novel neuropeptide encoded by the calcitonin gene via tissue-specific RNA processing", Nature, 1983, 304:129-135.

Rudolf, K., et al., "Development of Human Calcitonin Gene-Related Peptide (CGRP) Receptor Antagonists. 1. Potent and Selective Small Molecule CGRP Antagonists. 1-[$N^2$-[3,5-Dibromo-$N$-[[4-(3,4-dihydro-2(1$H$)-oxoquinazolin-3-yl)-1-piperidinyl]carbonyl]-D-tyrosyl] L-lysyl]-4-(4-pyridinyl)piperazine: The First CGRP Antagonist for Clinical Trials in Acute Migraine", J. Med. Chem. 2005, 48: 5921-5931.

Shen, Y-T. et al., "Functional Role of α-Calcitonin Gene-Related Peptide in the Regulation of the Cardiovascular System", J. Pharm. Exp. Ther., 2001, 298: 551-558.

Van Valen, F. et al., "Calcitonin gene-related peptide (CGRP) receptors are linked to cyclic adenosine monophosphate production in SK-N-MC human neuroblastoma cells", Neuroscience Letters, 1990, 119: 195-198.

Williamson, D.J. and Hargreaves, R.J., "Neurogenic Inflammation in the Context of Migraine", *Microsc. Res. Tech.,* 2001, 53: 167-178.

Williamson, D.J., et al., "Intravital microscope studies on the effects of neurokinin agonists and calcitonin gene-related peptide in dural vessel diameter in the anaesthetized rat," *Cephalalgia,* 1997, 17: 518-524.

Williamson, D.J., et al., "Sumatriptan inhibits neurogenic vasodilation of dural blood vessels in the anaesthetized rat-intravital microscope studies," *Cephalalgia,* 1997, 17: 525-531.

Xin, Z., et al., "Potent, Selective Inhibitors of Protein Tyrosine Phosphatase IB", *Bioorg. Med. Chem. Lett.,* 2003, 13: 1887-1890.

* cited by examiner

CGRP ANTAGONISTS

CROSS-REFERENCE TO RELATED APPLICATIONS

This is a non-provisional application which claims the benefit of U.S. Provisional Application Ser. No. 60/711,294 filed Aug. 25, 2005.

BACKGROUND OF THE INVENTION

Calcitonin gene-related peptide (CGRP) is a naturally occurring 37-amino-acid peptide first identified in 1982 (Amara, S. G. et al. *Science* 1982, 298, 240-244). Two forms of the peptide are expressed ($\alpha$CGRP and $\beta$CGRP) which differ by one and three amino acids in rats and humans, respectively. The peptide is widely distributed in both the peripheral (PNS) and central nervous system (CNS), principally localized in sensory afferent and central neurons, and displays a number of biological effects, including vasodilation.

When released from the cell, CGRP binds to specific cell surface G protein-coupled receptors and exerts its biological action predominantly by activation of intracellular adenylate cyclase (Poyner, D. R. et al. *Br J Pharmacol* 1992, 105, 441-7; Van Valen, F. et al. *Neurosci Lett* 1990, 119, 195-8.). Two classes of CGRP receptors, $CGRP_1$ and $CGRP_2$, have been proposed based on the antagonist properties of the peptide fragment CGRP(8-37) and the ability of linear analogues of CGRP to activate $CGRP_2$ receptors (Juaneda, C. et al. *TiPS* 2000, 21, 432-438). However, there is lack of molecular evidence for the $CGRP_2$ receptor (Brain, S. D. et al. *TiPS* 2002, 23, 51-53). The $CGRP_1$ receptor has three components: (i) a 7 transmembrane calcitonin receptor-like receptor (CRLR); (ii) the single transmembrane receptor activity modifying protein type one (RAMP1); and (iii) the intracellular receptor component protein (RCP) (Evans B. N. et al. *J Biol Chem.* 2000, 275, 31438-43). RAMP1 is required for transport of CRLR to the plasma membrane and for ligand binding to the CGRP-receptor (McLatchie, L. M. et al. *Nature* 1998, 393, 333-339). RCP is required for signal transduction (Evans B. N. et al. *J Biol Chem.* 2000, 275, 31438-43). There are known species-specific differences in binding of small molecule antagonists to the CGRP-receptor with typically greater affinity seen for antagonism of the human receptor than for other species (Brain, S. D. et al. *TiPS* 2002, 23, 51-53). The amino acid sequence of RAMP1 determines the species selectivity, in particular, the amino acid residue Trp74 is responsible for the phenotype of the human receptor (Mallee et al. *J Biol Chem* 2002, 277, 14294-8).

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. *CNS Drugs* 2001, 15(10), 745-53; Williamson, D. J. *Microsc. Res. Tech.* 2001, 53, 167-178.; Grant, A. D. *Brit. J Pharmacol.* 2002, 135, 356-362.). Serum levels of CGRP are elevated during migraine (Goadsby P. J. et al. *Ann. Neurol.* 1990, 28, 183-7) and treatment with anti-migraine drugs returns CGRP levels to normal coincident with alleviation of headache (Gallai V. et al. *Cephalalgia* 1995, 15, 384-90). Migraineurs exhibit elevated basal CGRP levels compared to controls (Ashina M. et al., *Pain* 2000, 86(1-2), 133-8). Intravenous CGRP infusion produces lasting headache in migraineurs (Lassen L. H. et al. *Cephalalgia.* 2002, 22(1), 54-61). Preclinical studies in dog and rat report that systemic CGRP blockade with the peptide antagonist CGRP(8-37) does not alter resting systemic hemodynamics nor regional blood flow (Shen, Y.-T. et al. *J Pharmacol. Exp. Ther.* 2001, 298, 551-8). Thus, CGRP-receptor antagonists may present a novel treatment for migraine that avoids the cardiovascular liabilities of active vasoconstriction associated with non-selective $5\text{-HT}_{1B/1D}$ agonists, "triptans" (e.g., sumatriptan).

There are various in vivo migraine models known in the literature (see De Vries, P. et al. *Eur. J Pharmacol.* 1999, 375, 61-74). Some electrically stimulate the trigeminal ganglion and measure dilation of the intracranial vessels which they innervate (e.g., Williamson et al. *Cephalalgia* 1997, 17, 518-24). Since facial arteries are also innervated by the trigeminal nerve, other models study changes in facial blood flow induced by electrical trigeminal activation (e.g., Escott et al. *Brain Res.* 1995, 669, 93). Alternatively, other peripheral nerves (e.g., saphenous) and vascular beds (e.g., abdominal blood flow) are also studied (e.g., Escott et al. *Br. J. Pharmacol.* 1993, 110, 772-6). All models have been shown to be blocked by pretreatment with the peptide antagonist CGPR (8-37) a peptide fragment that is absent the $1^{st}$ seven residues, or by a small molecule CGRP-receptor antagonist. In some instances, exogenous CGRP has been used as a stimulus. However, these models are all invasive terminal procedures, and none have shown the clinically important abortive effect of reversing an established increase in artery dilation or increased blood flow using post-treatment of a CGRP-receptor antagonist. Williamson used inter alia i.v. CGRP as a stimulus to increase intracranial dural artery diameter in sodium pentobarb anesthetized rats employing a terminal 'intravital' procedure that involved drilling to thin the skull and the creation of a closed cranial window to visualize dural arteries (Williamson et al. Cephalalgia 1997, 17, 518-24 and Williamson et al. Cephalalgia. 1997, 17, 525-31). The effect was blocked by pretreatment with i.v. CGRP(8-37). Escott inter alia drilled into the rat skull and used brain electrodes to electrically stimulate the trigeminal ganglion and measured laser Doppler facial blood flow in a terminal procedure in sodium pentobarb anesthetized rats involving neuromuscular blockade, tracheal intubation and artificial ventilation. The effect was blocked by pretreatment with CGRP(8-37) (Escott et al. Brain Res. 1995, 669, 93). Escott inter alia used intradermal (i.d.) CGRP as the stimulus to increase blood flow in rat abdominal skin of sodium pentobarb anesthetized animals outfitted with cannulated jugular veins for anesthetic and drug delivery. The effect was blocked by pretreatment with i.v. CGRP(8-37) (Escott et al. *Br. J. Pharmacol.* 1993, 110, 772-6). Chu used inter alia i.d. CGRP as the stimulus in rats and measured laser Doppler changes in blood flow in the skin of the back in a terminal method using sodium pentobarb anesthetized and tracheal cannulated animals; and showed pretreatment blockade by continuous release of CGRP(8-37) from subcutaneously (s.c.) implanted osmotic pumps (Chu et al. *Neurosci. Lett.* 2001, 310, 169-72). Hall inter alia used topical CGRP to increase hamster cheek pouch arteriole diameter and i.d. CGRP to increase blood flow in rat dorsal skin of sodium pentobarb anesthetized animals outfitted with cannulated jugular veins for anesthetic and drug delivery. The effect was blocked by pretreatment with i.v. CGRP(8-37) (Hall et al. *Br. J Pharmacol.* 1995, 114, 592-7 and Hall et al. *Br. J Pharmacol.* 1999, 126, 280-4). Doods inter alia drilled into the skull of the marmoset (new world monkey) and used brain electrodes to produce electrical stimulation of the trigeminal ganglion and measured facial blood flow in an invasive terminal procedure involving neuromuscular blockade and artificial ventilation of sodium pentobarbital anesthetized primates. Increase in flow was blocked by pre-treatment of a small molecule CGRP antagonist (Doods et al. *Br. J. Pharmacol.* 2000, 129(3),420-3). See also "Isolated DNA Molecules Encoding Humanized Calcitonin Gene-Related Peptide Receptor, Related Non-Human Transgenic Animals and Assay Methods" (WO 03/272252). Thus the method of the present invention procedure being inter alia a non-invasive survival model in primates measuring exogenous CGRP-induced changes in facial blood flow and demonstrating pre- and post-treatment effects of peptide and small molecule CGRP antagonists in spontaneously breathing isoflurane anesthetized marmosets who recover from the procedure offers significant advantages.

DESCRIPTION OF THE INVENTION

The invention encompasses compounds of formula I, pharmaceutically acceptable salts and solvates thereof, and compositions and methods of treatment using these compounds.

One aspect of the invention is a compound of formula I

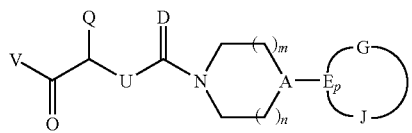

or a pharmaceutically acceptable salt or solvate thereof, wherein:

V is $(R^1)(R^2)NCOCH(R^4)NH$ where the carbon bearing $R^4$ has an absolute configuration of either R or S;

$R^4$ is hydrogen, $C_{1-6}$alkyl, or $C_{1-6}$alkyl substituted in the ω-position with amino, formylamino, $C_{1-6}$alkylamino, $C_{1-6}$dialkylamino, $C_{1-6}$alkoxycarbonylamino, $C_{1-6}$alkanoylamino, benzyloxycarbonylamino, hydroxy, mercapto, methylthio, 1-azetidinyl, 1-pyrrolidinyl, 1-piperidinyl, carboxy, carbamyl, guanidino, ureido, phenyl, hydroxyphenyl, indolyl, imidazolyl, naphthyl, or pyridinyl, wherein phenyl, hydroxyphenyl, indolyl, imidazolyl, naphthyl, and pyridinyl is further substituted with 0-2 substituents selected from the group consisting of halo, cyano, $C_{1-2}$alkyl, $C_{1-2}$alkoxy, $C_{1-2}$haloalkyl, or $C_{1-2}$haloalkoxy;

$R^1$ and $R^2$ are each independently $L^1$, wherein $L^1$ is selected from the group consisting of H, $C_{1-6}$alkyl, $C_{2-6}$alkenyl, $C_{2-6}$alkynyl, $[(C_{1-3}alkyl)_2amino]C_{1-6}$alkyl, $C_{3-7}$cycloalkyl, phenyl, azetidinyl, adamantyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino and dioxolanyl;

and $R^1$ and $R^2$ are each optionally and independently substituted with 1 or 2 of the same or different substituents selected from the group consisting of halo, cyano, $C_{1-4}$alkyl, $C_{1-4}$haloalkyl, $C_{1-4}$alkoxy, hydroxy, amino, $C_{3-7}$cycloalkyl, $C_{1-3}$alkylamino, $C_{1-3}$dialkylamino, $(C_{1-3}alkyl)_{0-2}$ureido, phenyl and benzyl; $R^1$ and $R^2$ optionally and independently contain 1 or 2 carbonyls wherein the carbon atom of said carbonyl is a member of the heterocycles comprising $R^1$ and $R^2$;

$L^1$ is optionally and independently interrupted from the nitrogen to which it is attached by $L^2$;

$L^2$ is independently $C_{1-3}$alkylene or $C_{1-3}$alkylidene;

or $R^1$ and $R^2$ together with the nitrogen to which they are attached form X, wherein X is azetidinyl, pyrrolyl, pyrrolinyl, pyrrolidinyl, imidazolinyl, imidazolidinyl, pyrazolinyl, pyrazolidinyl, azepinyl, diazepinyl, piperazinyl, piperidinyl, morpholino or thiomorpholino;

wherein X is optionally substituted with Y, wherein Y is dioxolanyl, $C_{1-9}$alkyl, $C_{2-9}$alkenyl, $C_{2-9}$alkynyl, $C_{1-4}$alkylamino, $C_{1-4}$dialkylamino, $C_{1-4}$alkoxy, $C_{3-7}$cycloalkyl, phenyl, azetidinyl, furanyl, thienyl, pyrrolyl, pyrrolinyl, pyrrolidinyl, pyrrolidinonyl, imidazolyl, imidazolinyl, imidazolidinyl, imidazolidinonyl, pyrazolyl, pyrazolinyl, pyrazolidinyl, azepinyl, diazepinyl, pyridyl, pyrimidinyl, dihydrobenzimidazolonyl, piperazinyl, piperidinyl, morpholino, benzothiazolyl, benzisothiazolyl or thiomorpholino;

and wherein X and Y are optionally interrupted with Z, wherein Z is NHC(O)O, NHC(O)NH, NC(O)NH$_2$, NH, $C_{1-3}$alkylene, $C_{1-3}$alkylene, $C_{1-3}$alkenylene-NHC(O)O—$C_{1-3}$alkylene; and optionally and independently substituted with 1 or 2 of the same or different substituents selected from the group consisting of $C_{1-4}$alkyl, amino, $C_{1-3}$alkylamino, $[(C_{1-3}alkyl)_2amino]C_{1-6}$alkyl, $(C_{1-3}alkyl)_{0-2}$ureido, phenyl and benzyl;

X and Y optionally and independently contain 1 or 2 carbonyls wherein the carbon atom of said carbonyl is a member of the heterocycles comprising X and Y;

provided that if X is substituted with Y, and if X and Y are not interrupted with Z, then X and Y optionally share one carbon atom and together form a spirocyclic moiety;

Q is Q' or Q";

wherein

Q' is $(S^y)_sR^3$; and

Q" is $NH(S^y)_sR^3$, $NHC(O)(S^y)_sR3$, $NHC(O)O(S^y)_sR^3$, $NHC(O)NH(S^y)_sR^3$, $O(S^y)_sR^3$, $(S^y)_sNHR^3$, $(S^y)_sNHC(O)R^3$, $(S^y)_sNHC(O)OR^3$, $(S^y)_sNHC(O)NHR^3$ or $(S^y)_sOR^3$; wherein $S^y$ is $C_{1-3}$alkylene or $C_{1-3}$alkylidene and s is 0 or 1;

U is $CH_2$, O, or NH, provided that if Q is Q", then U is $CH_2$;

$R^3$ is a heterocycle having two fused rings with 5 to 7 members in each of said rings, said heterocycle containing one to five of the same or different heteroatoms selected from the group consisting of O, N and S and said heterocycle optionally containing 1 or 2 carbonyls wherein the carbon atom of said carbonyl is a member of said fused rings;

or $R^3$ is a 4 to 6 membered heterocycle containing one to three of the same or different heteroatoms selected from the group consisting of O, N and S, optionally containing 1 to 2 carbonyls, wherein the carbon atom of said carbonyl is a member of said 4 to 6 membered heterocycle;

or $R^3$ is $C_{3-7}$cycloalkyl;

or $R^3$ is carbazolyl, fluorenyl, phenyl, phenoxy, $(C_{1-4})$phenylalkoxy, or napthyl; or or $R^3$ is $C_{1-8}$alkyl, $C_{2-7}$alkenyl, $C(O)R^{3'}$, $CHC(O)OR^{3'}$, $CH(CH_3)C(O)OR^{3'}$, $C(O)OR^{3'}$ or $C_{2-7}$alkynyl;

and wherein $R^3$ is optionally substituted with 1 to 3 of the same or different substituents selected from the group consisting of benzyl, phenyl, phenoxy, ($C_{1-4}$)phenylalkoxy, ($C_{1-3}$)benzoylalkyl, cyano, amino, nitro, halo, $C_{1-6}$alkyl, ($C_{1-3}$)haloalkyl, ($C_{1-3}$)haloalkoxy, ($C_{1-3}$)alkylamine, ($C_{1-3}$)dialkylamine, $OR^{3'}$, $C(O)R^{3'}$, $C(O)OR^{3'}$, $OC(O)R^{3'}$, $N(R^{3'})_2$, $C(O)N(R^{3'})_2$, $N(R^{3'})C(O)(R^{3'})_2$, $N(R^{3'})C(O)N(R^{3'})_2$, $N(R^{3'})C(O)OR^{3'}$, $OC(O)N(R^{3'})_2$, $N(R^{3'})SO_2R^{3'}$, $SO_2N(R^{3'})_2$ and $SO_2R^{3'}$;

$R^{3'}$ is H or $C_{1-6}$alkyl, provided that if $R^{3a}$ is $C(O)R^{3'}$, $CHC(O)OR^{3'}$, $CH(CH_3)C(O)OR^{3'}$ or $C(O)OR^{3'}$, then said $C(O)R^{3'}$, $CHC(O)OR^{3'}$, $CH(CH_3)C(O)OR^{3'}$ or $C(O)OR^{3'}$ are unsubstituted;

D is O, NCN or $NSO_2C_{1-3}$alkyl;

A is C, N or CH;

m and n are independently 0, 1 or 2, provided that if m and n are 0, then A is not N; if m is 2, then n is not 2; or if n is 2, then m is not 2;

E is N, CH or C;

p is 0 or 1;

if p is 1, then G, J and E together form $A^x$ or $A^y$;

$A^x$ is a fused heterocycle having two fused rings with 5 to 7 members in each of said rings, said heterocycle containing one to four of the same or different heteroatoms selected from the group consisting of O, N and S and optionally containing 1 or 2 carbonyls wherein the carbon atom of said carbonyl is a member of said fused heterocycle;

$A^y$ is a 4 to 6 membered heterocycle containing one to three heteroatoms selected from the group consisting of O, N and S and optionally containing 1 to 2 carbonyls, wherein the carbon atom of said carbonyl is a member of said 4 to 6 membered heterocycle;

wherein $A^x$ and $A^y$ are optionally substituted with $C_{1-4}$alkyl, $C_{1-4}$alkoxy, $C_{1-4}$haloalkyl, cyano, $C_{3-7}$cycloalkyl, phenyl, halophenyl, halo, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl or morpholino; or if p is 0 such that G and J are each attached to A, then A is C, and G, J and A together form a spirocyclic ring system with said rings of said system containing A and wherein G, J and A together are $A^x$ or $A^y$.

Another aspect of the invention is a compound of Formula I where the carbon bearing $R^4$ is of the (S) configuration.

Another aspect of the invention is a compound of Formula I where the carbon bearing $R^4$ is of the (R) configuration.

Another aspect of the invention is a compound of Formula I where X is piperazinyl or piperidinyl and Y is pyridinyl or piperidinyl.

Another aspect of the invention is a compound of Formula I where $R^4$ is $C_{1-6}$alkyl substituted in the ω-position with amino, formylamino, $C_{1-6}$alkylamino, $C_{1-6}$dialkylamino, $C_{1-6}$alkoxycarbonylamino, $C_{1-6}$alkanoylamino, or benzyloxycarbonylamino.

Another aspect of the invention is a compound of Formula I where $R^4$ is aminobutyl or (t-butoxycarbonylamino)butyl.

Another aspect of the invention is a compound of Formula I where Q is $(S^y)R^3$.

Another aspect of the invention is a compound of Formula I where Q is (indazolyl)methyl, (benzotriazolyl)methyl or (benzoxazolinonyl)methyl optionally substituted with 1 to 3 of the same or different substituents selected from the group consisting of halo, cyano, or $C_{1-2}$alkyl, or $C_{1-2}$halolkyl.

Another aspect of the invention is a compound of Formula I where U is NH.

Another aspect of the invention is a compound of Formula I where D is O.

Another aspect of the invention is a compound of Formula I where A is CH.

Another aspect of the invention is a compound of Formula I where A is N.

Another aspect of the invention is a compound of Formula I where m and n are 1.

Another aspect of the invention is a compound of Formula I where G, J, and E are $A^x$.

The description of the invention herein should be construed in congruity with the laws and principals of chemical bonding. For example, it may be necessary to remove a hydrogen atom in order accommodate a substitutent at any given location.

As used herein, "heterocyclic" or "heterocycle" includes cyclic moieties containing one or more heteroatoms, (e.g., O, N or S) said heterocycles include those that are aromatic and those that are not, i.e., "alicyclic", unless otherwise specified.

As used herein, the term "fused bicyclic system" when describing for example a 5,6-fused bicyclic system containing 1 to 4 nitrogen atoms includes aromatic and alicyclic systems, e.g. indolizine, indole, isoindole, 3H-indole, indoline, indazole or benzimidazole.

If a substituent is named generically, then any and all species of that genus comprise that aspect of the invention. For example, a substituent generically named as "pyrrolonyl" (the radical of "pyrrolone", a pyrrole having a carbonyl) includes pyrrol-2-onyls wherein the carbonyl is adjacent to the nitrogen and pyrrol-3-onyls wherein the carbonyl and nitrogen have an intervening methylene.

Similarly, the present invention comprises that a substituent may be attached at any and all suitable points of attachement on said substituent unless otherwise specified.

However, it is also understood that the compounds encompassed by the present invention are those that are chemically stable, i.e., heteroalicyclic substituents of the present invention should not be attached in such a way that a heteroatom in said heteroalicyclic substituent is alpha to a point of attachment wherein said point of attachment is also a heteroatom.

An embodiment or aspect which depends from another embodiment or aspect, will describe only the variables having values or provisos that differ from the embodiment or aspect from which it depends. If for example a dependent embodiment only addresses $R^2$, then the variables and provisos not related to $R^2$ should reflect that of the embodiment from which it depends.

If a variable is quantified with a value of zero, then a bond attaching said variable should no longer be represented.

As used herein, "alkylene" means a divalent alkane, i.e., an alkane having two hydrogen atoms removed from said alkane (said hydrogen removed from two different carbon atoms when said alkane contains more than one carbon atom), e.g., —$CH_2CH_2CH_2$—.

As used herein, "alkylidene" means an alkane having two hydrogen atoms removed from one carbon atom in said alkane, e.g.,

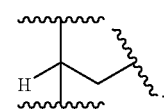

It should be understood that the alternating double bond designations in the six-membered ring of the 5,6-membered fused structure represented in Formula (I) are relative and represent the delocalized π orbital electrons of said ring.

As used herein, "aryl" or "ar-" includes phenyl or napthyl.

As used herein, "heterocyclic" or "heterocyclo" includes both heteroaryl and heteroalicyclic.

As used herein, "halo" or "halogen" includes fluoro, chloro, bromo and iodo and further means one or more of the same or different halogens may be substituted on a respective moiety.

Unless specificied otherwise, acyclic hydrocarbons such as alkyl, alkoxy, alkenyl and alkynyl may be branched or straight chained.

It is to be understood that the present invention may include any and all possible stereoisomers, geometric isomers, diastereoisomers, enantiomers, anomers and optical isomers, unless a particular description specifies otherwise.

As used herein, "Trp74", means that the 74$^{th}$ residue in RAMP1 is tryptophan (Mallee et al. *J Biol Chem* 2002, 277, 14294-8) incorporated by reference herein.

As used herein "anti-migraine compound" includes any compound, peptide or peptide fragment (modified or unmodified) capable of reversing or attenuating CGRP-receptor mediated vasodilation, (e.g., CGRP-receptor antagonists).

As used herein "test compound" includes any compound, peptide or peptide fragment (modified or unmodified) being tested to determine if it is capable of reversing or attenuating CGRP-receptor mediated vasodilation, (e.g., putative CGRP-receptor antagonists).

As used herein, "CGRP-receptor agonist" includes any compound, peptide or peptide fragment (modified or unmodified) capable of inducing CGRP-receptor mediated vasodilation particularly by example αCGRP or βCGRP; other members of the calcitonin family, e.g, adrenomedullin; N-terminal CGRP fragments, e.g, CGRP(1-12) CGRP(1-15) and CGRP (1-22); C-terminal amide (NH2) versions of CGRP e.g., CGRP(1-8+NH2), CGRP(1-13+NH2) or CGRP(1-14+NH2); and non-naturally occurring CGRP analogues e.g., [Ala$^1$ψ(CH2NH)Cys$^2$]hCGRP which contains a pseudopeptide bond between Ala$^1$ and Cys$^2$. See Maggi C A, Rovero P, Giuliani S, Evangelista S, Regoli D, Meli A. Biological activity of N-terminal fragments of calcitonin gene-related peptide. Eur J Pharmacol. Apr. 10, 1990; 179(1-2):217-9; Qing X, Wimalawansa S J, Keith I M. Specific N-terminal CGRP fragments mitigate chronic hypoxic pulmonary hypertension in rats. Regul Pept. Jan. 31, 2003; 110(2):93-9; and Dennis T, Fournier A, St Pierre S, Quirion R. Structure-activity profile of calcitonin gene-related peptide in peripheral and brain tissues. Evidence for receptor multiplicity. J Pharmacol Exp Ther. November 1989; 251(2):718-25 incorporated by reference herein.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention also includes all solvated forms of the compounds, particularly hydrates. Solvates do not contribute significantly to the physiological activity or toxicity of the compounds and as such function as pharmacological equivalents. Solvates may form in stoichiometric amounts or may form from adventitious solvent or a combination of both. One type of solvate is hydrate, and some hydrated forms include monohydrate, hemihydrate, and dihydrate.

Some of the compounds of the invention possess asymmetric carbon atoms, such as the carbon atom bearing Q in the formula below. The invention includes all stereoisomeric forms including enantionmers, diastereomers, and mixtures thereof. Stereoisomeric mixtures of the compounds and related intermediates can be separated into individual isomers according to methods commonly known in the art.

Synthetic Methods

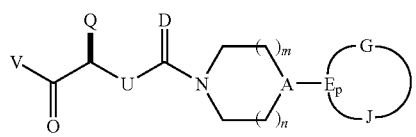

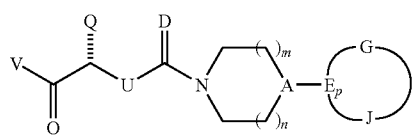

Several methods for preparing Formula I compounds are illustrated in the following schemes and examples. Some of the compounds described can be synthesized according to Scheme 1 or Scheme 2. Starting materials are commercially available or known in the art. Variations of the compounds and the procedures to make them which are not illustrated are also known in the art. The designation of chemical substituents and variables in this section is for illustrative purposes only and should not be confused with structural variables in the claims or in other sections of the specification.

Scheme 1 describes how to make some Formula I compounds. Hydrogenolysis of (R)-methyl 2-(benzyloxycarbonyl)-3-(7-methyl-1H-indazol-5-yl)propanoate to give (R)-methyl 2-amino-3-(7-methyl-1H-indazol-5-yl)propanoate (I) can be accomplished with 10% palladium on carbon. Amines I and II can be used to make ureas with N,N'-disuccinimidyl carbonate or related reagents. Carboxylic esters (III) can be hydrolyzed to acids under mild conditions mediated by aqueous lithium hydroxide to give acid (IV). Amine V can be synthesized from a natural or unnatural amino acid and a base such as 4-pyridyl piperidine in presence of coupling agent using the methods described (The Practice of Peptide Synthesis by Bodansky and Bodansky). The acid (IV) and amine (V) readily couple in presence of 2-(1H-benzotriazole-1-yl)-1,1,3,3-tetramethyluronium tetrafluoroborate to give amide (VI). Treatment of amide (VI) with trifluoroacetic acid would furnish the desired compound (VII).

Scheme 1.

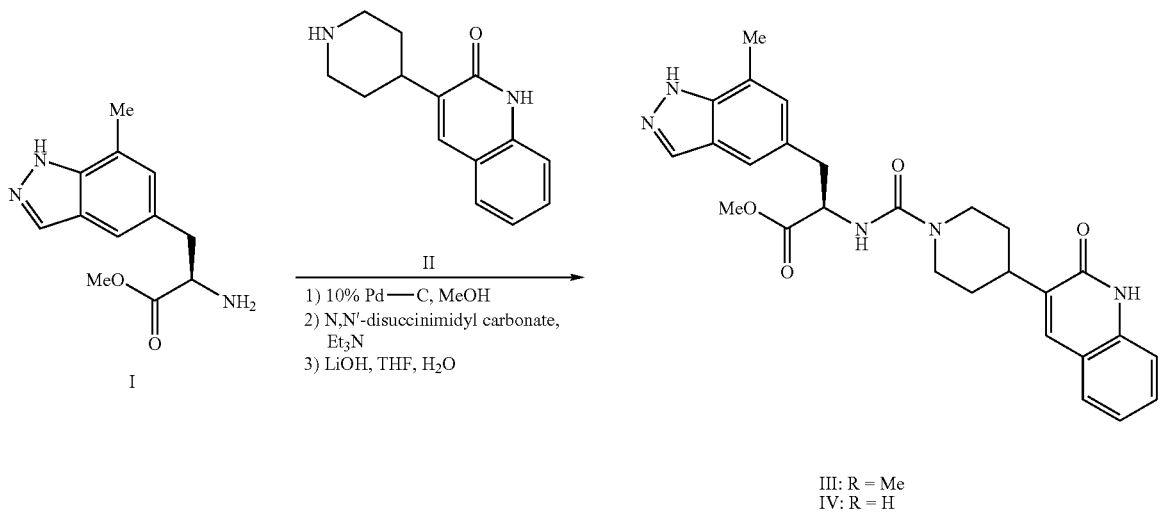

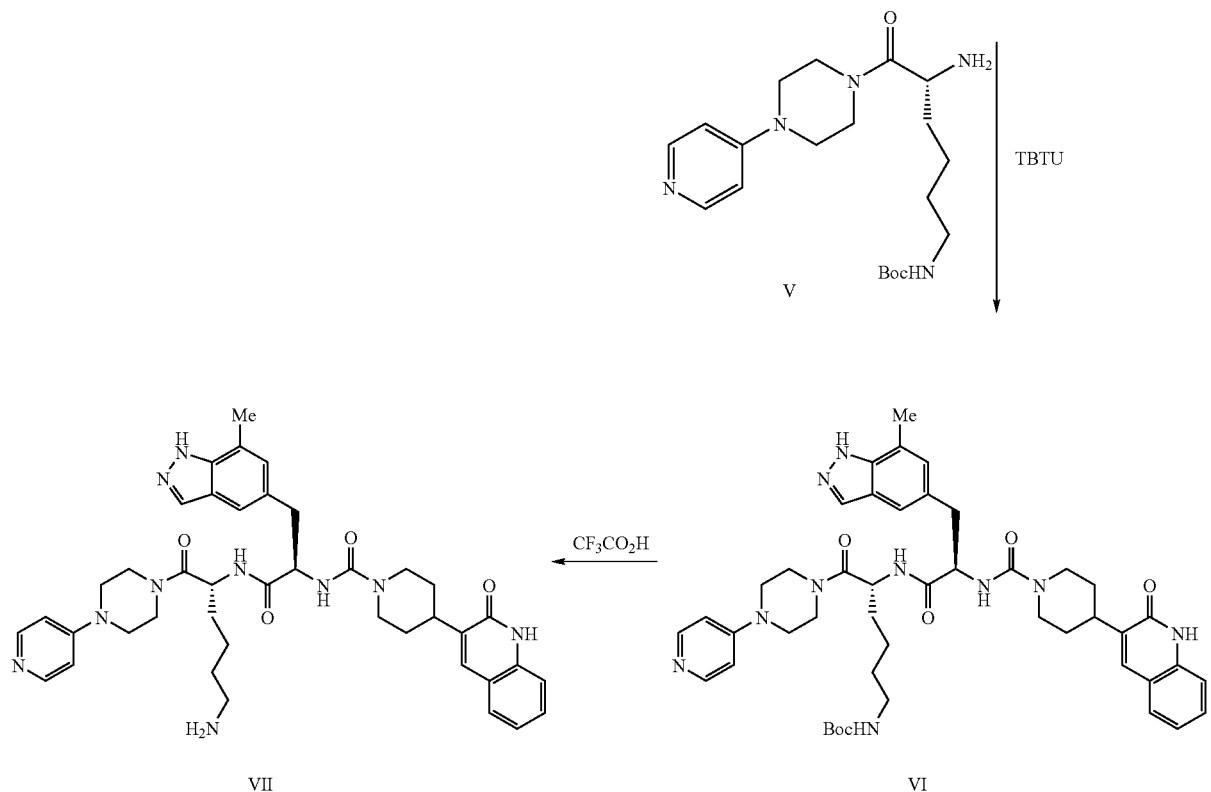

Alternatively, some Formula I compounds can also be prepared using Scheme 2. Treatment of amine (V) with carboxylic acid (VIII) under 2-(1H-benzotriazole-1-yl)-1,1,3,3-tetramethyluronium tetrafluoroborate mediated coupling conditions can provide amide (IX). The benzyloxycarbonyl protecting group can be deprotected under hydrogenolysis conditions to provide the amine (X). Amines X and II can react with N,N'-disuccinimidyl carbonate to provide urea (VI) which can be deprotected with TFA to provide the desired compound.

Scheme 2.

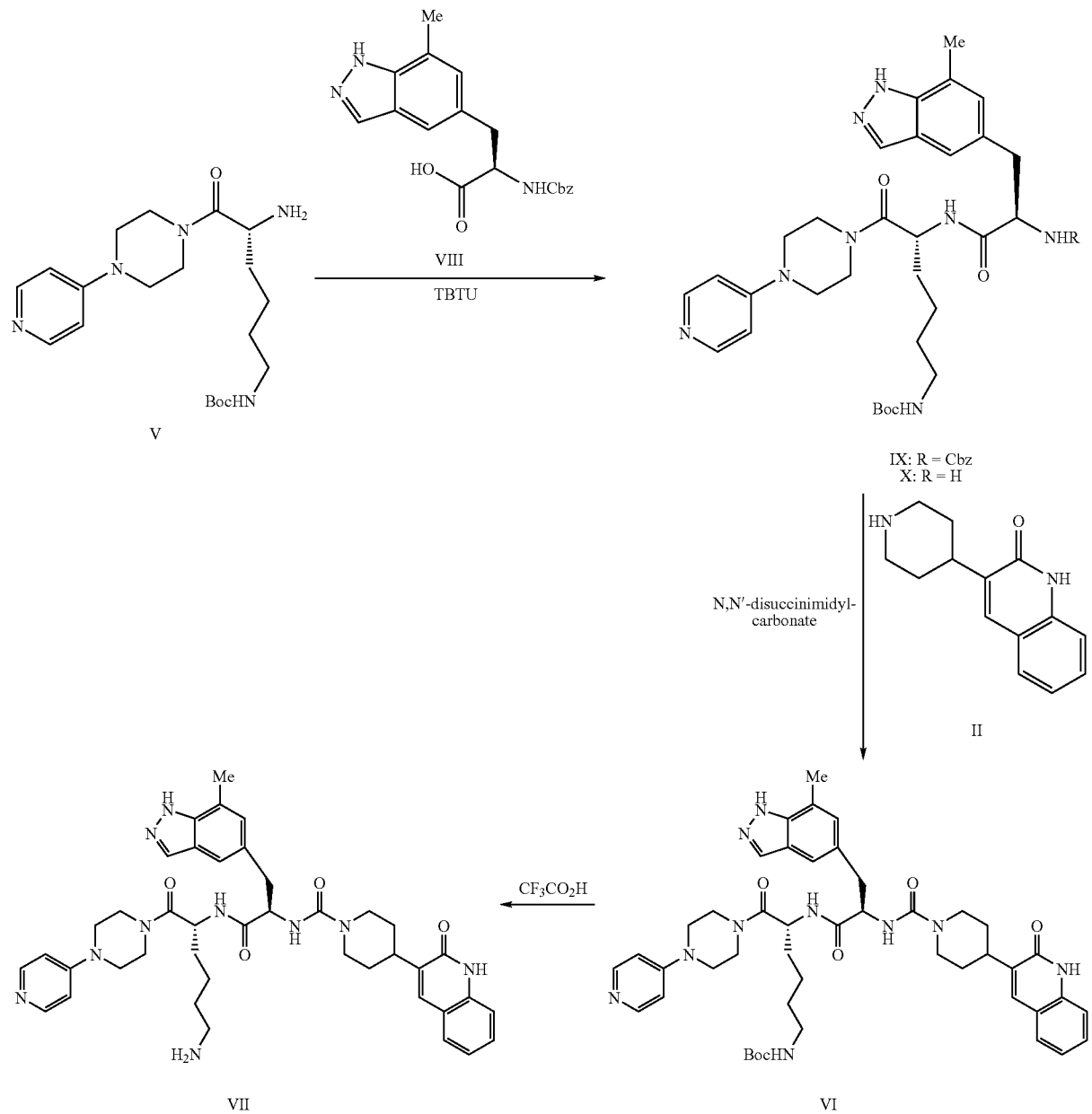

Biological Methods

The compounds of Formula I are antagonists of the CGRP receptor as demonstrated in the following assay.

CGRP radioligand binding assay. Tissue Culture. SK-N-MC cells were grown at 37° C. in 5% $CO_2$ as a monolayer in medium consisting of MEM with Earle's salts and L-glutamine (Gibco) supplemented with 10% fetal bovine serum (Gibco).

Cell Pellets. The cells were rinsed twice with phosphate-buffered saline (155 mM NaCl, 3.3 mM $Na_2HPO_4$, 1.1 mM $KH_2PO_4$, pH 7.4), and incubated for 5-10 min. at 4° C. in hypotonic lysis buffer consisting of 10 mM Tris (pH 7.4) and 5 mM EDTA. The cells were transferred from plates to polypropylene tubes (16×100 mm) and homogenized using a polytron. Homogenates were centrifuged at 32,000×g for 30 min. The pellets were resuspended in cold hypotonic lysis buffer with 0.1% mammalian protease inhibitor cocktail (Sigma) and assayed for protein concentration. The SK-N-MC homogenate was then aliquoted and stored at −80° C. until needed.

Binding Assay. The compounds of invention were solubilized and carried through serial dilutions using 100% DMSO. Aliquots from the compound serial dilutions were further diluted 25 fold into assay buffer (50 mM Tris-Cl pH 7.5, 5 mM $MgCl_2$, 0.005% Triton X-100) and transferred (volume 50 µl) into 96 well assay plates. [$^{125}$I]-CGRP (Amersham Biosciences) was diluted to 60 pM in assay buffer and a volume of 50 μl was added to each well. SK-N-MC pellets were thawed, diluted in assay buffer with fresh 0.1% mammalian protease inhibitor cocktail (Sigma), and homogenized again. SK-N-MC homogenate (5 μg/well) was added in a volume of 100 μl. The assay plates were then incubated at room temperature for 2 h. Assays were stopped by addition of excess cold wash buffer (20 mM Tris-Cl pH 7.5, 0.1% BSA) immediately followed by filtration over glass fiber filters (Whatman GF/B) previously soaked in 0.5% PEI. Non-specific binding was defined with 1 μM beta-CGRP. Protein bound radioctivity was determined using a gamma or scintillation counter. The $IC_{50}$ was defined as the concentration of a compound of invention required to displace 50% of radioligand binding. Results are tabulated in Table 1 as follows: 0.01 nM≦A≦10 nM; 10 nM<B≦100 nM; 100 nM<C≦1000 nM; D>1000 nM.

TABLE 1

Pharmaceutical Compositions and Methods of Treatment

| Example | CGRP $IC_{50}$ (nM) |
|---|---|
| 1 | * |
| 2 | A |
| 3 | A |
| 4 | A |
| 5 | A |
| 6 | A |
| 7 | A |
| 8 | A |
| 9 | A |

The compounds of Formula I inhibit the CGRP receptor. As such they are useful for treating disorders associated with aberrant CGRP levels or where modulating CGRP levels may have therapeutic benefit.

Accordingly, another aspect of the invention is a pharmaceutical composition comprising a compound of Formula I with a pharmaceutically acceptable adjuvant, carrier, or diluent.

Compounds are generally given as pharmaceutical compositions comprised of a therapeutically effective amount of a compound of Formula I, or a pharmaceutically acceptable salt, and a pharmaceutically acceptable carrier and may contain conventional exipients. A therapeutically effective amount is the amount needed to provide a meaningful patient benefit as determined by practitioners in that art. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Solid compositions may by formed in timed or sustained released formulations. Compositions are made using common formulation techniques and conventional excipients (such as binding and wetting agents) and vehicles (such as water and alcohols).

Solid compositions are normally formulated in dosage units providing from about 1 to about 1000 mg of the active ingredient per dose. Some examples of solid dosage units are 0.1 mg, 1 mg, 10 mg, 100 mg, 500 mg, and 1000 mg. Liquid compositions are generally in a unit dosage range of 1-100 mg/mL. Some examples of liquid dosage units are 0.1 mg/mL, 1 mg/mL, 10 mg/mL, 25 mg/mL, 50 mg/mL, and 100 mg/mL.

The invention encompasses all conventional modes of administration including oral, parenteral, intranasal, sublingual, and transdermal methods. Typically, the daily dose will be 0.01-100 mg/kg body weight daily. Generally, more compound is required orally and less parenterally. The specific dosing regime, however, should be determined by a physician using sound medical judgement.

Another aspect of the invention relates to a method of treating inflammation (particularly neurogenic inflammation), headache (particularly migraine), pain, thermal injury, circulatory shock, diabetes, Reynaud's syndrome, peripheral arterial insufficiency, subarachnoid/cranial hemorrhage, tumor growth, flushing associated with menopause and other conditions the treatment of which can be effected by the antagonism of the CGRP receptor by the administration of pharmaceutical compositions comprising compounds of Formula (I) as defined herein.

Another aspect of the invention relates to methods selected from the group consisting of (a) immune regulation in gut mucosa (b) protective effect against cardiac anaphylactic injury (c) stimulating or preventing interleukin-1b(IL-1b)-stimulation of bone resorption (d) modulating expression of NK1 receptors in spinal neurons and (e) airway inflammatory diseases and chronic obstructive pulmonary disease including asthma. See (a) Calcitonin Receptor-Like Receptor Is Expressed on Gastrointestinal Immune Cells. Hagner, Stefanie; Knauer, Jens; Haberberger, Rainer; Goeke, Burkhard; Voigt, Karlheinz; McGregor, Gerard Patrick. Institute of Physiology, Philipps University, Marburg, Germany. Digestion (2002), 66(4), 197-203; (b) Protective effects of calcitonin gene-related peptide-mediated evodiamine on guinea-pig cardiac anaphylaxis. Rang, Wei-Qing; Du, Yan-Hua; Hu, Chang-Ping; Ye, Feng; Tan, Gui-Shan; Deng, Han-Wu; Li, Yuan-Jian. School of Pharmaceutical Sciences, Department of Pharmacology, Central South University, Xiang-Ya Road 88, Changsha, Hunan, Naunyn-Schmiedeberg's Archives of Pharmacology (2003), 367(3), 306-311; (c) The experimental study on the effect calcitonin gene-related peptide on bone resorption mediated by interleukin-1. Lian, Kai; Du, Jingyuan; Rao, Zhenyu; Luo, Huaican. Department of Orthopedics, Xiehe Hospital, Tongji Medical College, Huazhong University of Science and Technology, Wuhan, Peop. Rep. China. Journal of Tongji Medical University (2001), 21(4), 304-307, (d) Calcitonin gene-related Peptide regulates expression of neurokininl receptors by rat spinal neurons. Seybold V S, McCarson K E, Mermelstein P G, Groth R D, Abrahams L G. J. Neurosci. 2003 23 (5): 1816-1824. epartment of Neuroscience, University of Minnesota, Minneapolis, Minn. 55455, and Department of Pharmacology, Toxicology, and Therapeutics, University of Kansas Medical Center, Kansas City, Kans. 66160 (e) Attenuation of antigen-induced airway hyperresponsiveness in CGRP-deficient mice. Aoki-Nagase, Tomoko; Nagase, Takahide; Oh-Hashi, Yoshio; Shindo, Takayuki; Kurihara, Yukiko; Yamaguchi, Yasuhiro; Yamamoto, Hiroshi; Tomita, Tetsuji; Ohga, Eijiro; Nagai, Ryozo; Kurihara, Hiroki; Ouchi, Yasuyoshi. Department of Geriatric Medicine, Graduate School of Medicine, University of Tokyo, Tokyo, Japan. American Journal of Physiology (2002), 283(5,Pt. 1), L963-L970; (f) Calcitonin gene-related peptide as inflammatory mediator. Springer, Jochen; Geppetti, Pierangelo; Fischer, Axel; Groneberg, David A. Charite Campus-Virchow, Department of Pediatric Pneumology and Immunology, Division of Allergy Research, Humboldt-University Berlin, Berlin, Germany. Pulmonary Pharmacology & Therapeutics (2003), 16(3), 121-130; and (g) Pharmacological targets for the inhibition of neurogenic inflammation. Helyes, Zsuzsanna; Pinter, Erika; Nemeth, Jozsef; Szolcsanyi, Janos. Department of Pharmacology and Pharmacotherapy, Faculty of Medicine, University of Pecs, Pecs, Hung.

Current Medicinal Chemistry: Anti-Inflammatory & Anti-Allergy Agents (2003), 2(2), 191-218 all incorporated by reference herein.

Another aspect of this invention relates to a method are provided combinations of the compounds of the present invention with one or more agents selected from the group consisting of COX-2 inhibitors, NSAIDS, aspirin, acetaminophen, triptans, ergotamine and caffeine for the treatment of migraine.

DESCRIPTION OF SPECIFIC EMBODIMENTS

The following examples are provided so that the invention might be more fully understood. These examples are illustrative only and should not be construed as limiting the invention in any way.

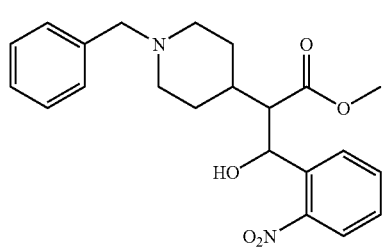

Intermediate 1

Methyl 2-(1-benzylpiperidin-4-yl)-3-hydroxy-3-(2-nitrophenyl)propanoate. Diisopropylamine (24.87 mmoles; 3.50 mL) was dissolved in tetrahydrofuran (30.00 mL). Mixture was cooled to −78° C. 2.5 M butyllithium in pentane (24.50 mmoles; 9.80 mL) was added to the mixture drop-wise. Reaction was stirred at −78° C. for 15 minutes. A solution of methyl 2-(1-benzylpiperidin-4-yl)acetate (22.24 mmoles; 5.50 g) in 8 mL THF was then added to the mixture dropwise over 20 minutes. Reaction stirred at −78° C. for 45 minutes. A solution of 2-nitrobenzaldehyde (24.48 mmoles; 3.70 g) in 5 mL THF was then added to the mixture dropwise over 15 minutes. Reaction was stirred at −78° C. for 30 minutes. Reaction was quenched with saturated aqueous ammonium chloride. Mixture was warmed to room temperature. Extracted from the mixture 2× EtOAc. Combined organics were dried (magnesium sulfate), filtered, then concentrated. Silica gel chromatography afforded the desired product in 89% yield as light yellow foam. MS m/e (M+H)$^+$=399.3.

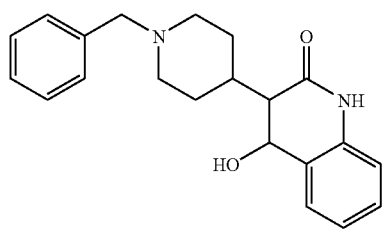

Intermediate 2

3-(1-benzylpiperidin-4-yl)-4-hydroxy-3,4-dihydroquinolin-2(1H)-one. Methyl 2-(1-benzylpiperidin-4-yl)-3-hydroxy-3-(2-nitrophenyl)propanoate (2.4 mmol, 950 mg) was dissolved in acetic acid (20 mL). Iron (17.7 mmol, 1.0 g) was added to the mixture. Reaction was heated at 85° C. and held with stirring for 1.5 hours. Mixture was cooled to room temperature then diluted with water (30 mL). Solids were decanted off. The aqueous solution was concentrated in vacuo. Residue was treated with ethyl acetate (50 mL). The mixture was made basic with aqueous sodium hydroxide. Celite was added to the resulting suspension to create a slurry. Mixture was filtered. Filtrate layers were separated. Aqueous layer was extracted 1× ethyl acetate. Combined organic layers were dried (magnesium sulfate), filtered and concentrated in vacuo. Title compound was obtained without further purification as yellow oil in 69% yield. MS m/e (M+H)$^+$=335.3.

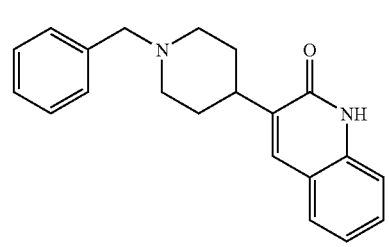

Intermediate 3

3-(1-benzylpiperidin-4-yl)quinolin-2(1H)-one. 3-(1-Benzylpiperidin-4-yl)-4-hydroxy-3,4-dihydroquinolin-2(1H)-one (1.6 mmol, 550 mg) was suspended in benzene (10 mL). p-Toluenesulfonic acid monohydrate (1.9 mmol, 370 mg) was added to the mixture. Reaction was heated to reflux and held for 1 hour. Reaction mixture was concentrated in vacuo. Residue was dissolved in 10% ethanol-dichloromethane (50 mL). Mixture was washed 2× with aqueous sodium bicarbonate. Organic layer was dried (magnesium sulfate), filtered and concentrated in vacuo. Residue was triturated with diethyl ether. Solids were filtered off, washed with diethyl ether, then dried in vacuo. Title compound was obtained as off-white solid in 63% yield. $^1$H NMR (300 MHz, DMSO-d$_6$): δ=11.72 (s, 1H), 7.72 (s, 1H), 7.62 (d, J=6.95, 1H), 7.47-7.38 (m, 1H), 7.35-7.30 (m, 4H), 7.29-7.20 (m, 2H), 7.14 (t, J=7.50, 1H), 3.49 (s, 3H), 2.92 (d, J=11.34, 2H), 2.83-2.69 (m, 1H), 2.04 (t, J=10.61, 2H), 1.78 (d, J=12.08, 2H), 1.71-1.47 (m, 2H). MS m/e (M+H)$^+$=319.3.

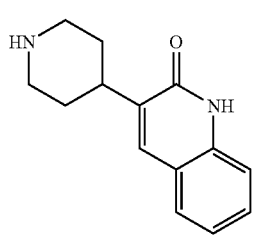

Intermediate 4

3-(Piperidin-4-yl)quinolin-2(1H)-one. 3-(1-benzylpiperidin-4-yl)quinolin-2(1H)-one (5.40 mmol, 1.72 g) was suspended in methanol (70 mL). A catalytic amount of 20% palladium hydroxide on carbon was added to the mixture. The reaction vessel was placed on a Parr apparatus and charged with 55 psi of hydrogen gas. Reaction shook at room temperature for 5 hours. Mixture was removed from the apparatus and filtered. Filtrate was concentrated. Title compound was obtained as white solid in 90% yield. $^1$H NMR (300 MHz, DMSO-d$_6$): δ=7.65 (s, 1H), 7.64 (d, J=10.61, 1H), 7.41 (t, J=7.50, 1H), 7.26 (d, J=8.05, 1H), 7.13 (t, J=7.32, 1H), 3.02

(d, J=11.71, 2H), 2.82 (t, J=11.89, 2H), 2.58 (t, J=11.71, 2H), 1.73 (t, J=11.71, 2H), 1.42 (m, 2H). MS m/e (M+H)+=229.4.

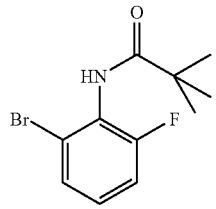

Intermediate 5

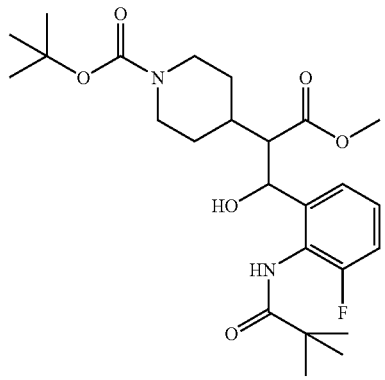

Intermediate 7

N-(2-Bromo-6-fluorophenyl)pivalamide. 2-Bromo-6-fluoroaniline (43.2 mmol, 8.2 g) was dissolved in pyridine (124 mmol, 10 mL). Pivaloyl chloride (57.15 mmol, 7.0 mL) was added to the mixture. Reaction was stirred at room temperature for 3 hours. Reaction mixture was concentrated in vacuo. Residue was treated with ethyl acetate (50 mL). Mixture was washed 2×1N HCl, 1× brine. Organic layer was dried (magnesium sulfate), filtered and concentrated in vacuo. Residue was treated with hexanes and triturated. Resulting solids were filtered off, washed with hexanes then dried in vacuo. Title compound was obtained as white solid in 76% yield. $^1$H NMR (300 MHz, CDCl$_3$): δ=7.39-7.31 (m, 1H), 7.14-7.03 (m, 2H), 6.98 (bs, 1H), 1.34 (s, 9H). MS m/e (M+H)+=274.1, 276.1.

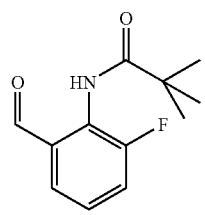

Intermediate 6

N-(2-Fluoro-6-formylphenyl)pivalamide. N-(2-Bromo-6-fluorophenyl)pivalamide (25.5 mmol, 7.0 g) was dissolved in tetrahydrofuran (200 mL). Mixture was cooled to −78° C. 2M Butyllithium in cyclohexane (62.0 mmol, 31.0 mL) was added to the mixture drop-wise. Reaction mixture was held at −78° C. for 30 minutes. A solution of N,N-dimethylformamide (129 mmol, 10.0 mL) in tetrahydrofuran (30 mL) was added to the reaction mixture drop-wise. Reaction was held at −78° C. for 30 minutes. Reaction was quenched with aqueous ammonium chloride then the mixture was allowed to warm to room temperature. Mixture was extracted 2× ethyl acetate. Combined organic layers were dried (magnesium sulfate), filtered and concentrated. Silica gel chromatography afforded the desired product as white solid in 80% yield. $^1$H NMR (300 MHz, CDCl$_3$): δ=9.93 (d, J=1.83, 1H), 9.14 (bs, 1H), 7.56-7.50 (m, 1H), 7.42-7.25 (m, 2H), 1.34 (s, 9H). MS m/e (M+H)+=224.2.

tert-Butyl 4-(1-(3-fluoro-2-pivalamidophenyl)-1-hydroxy-3-methoxy-3-oxopropan-2-yl)piperidine-1-carboxylate. Diisopropylamine (24.2 mmol, 3.40 mL) was dissolved in tetrahydrofuran (70 mL). The mixture was cooled to −78° C. 2N Butyllithium in cyclohexane (24.40 mmoles, 12.20 mL) was added drop-wise to the reaction. The mixture was held at −78° C. with stirring on and held for 20 minutes. A solution of tert-butyl 4-(2-methoxy-2-oxoethyl)piperidine-1-carboxylate (20.21 mmoles, 5.20 g) in 15 mL tetrahydrofuran was added to the mixture drop-wise. The mixture was held at −78° C. with stirring on and held for 45 min. In a seperate flask, 60% Sodium hydride in mineral oil (24.25 mmoles, 970.00 mg) was washed with hexanes then suspended in tetrahydrofuran (50.00 mL). The mixture was cooled to 0° C. A solution of N-(2-Fluoro-6-formylphenyl)pivalamide (20.16 mmoles, 4.50 g) in 20 mL tetrahydrofuran was added to the mixture drop-wise. The mixture was held at 0° C. with stirring on and held for 1 hr. Aldehyde mixture was added to the ester mixture drop-wise over 1.25 hours. The mixture was held at −78° C. with stirring on and held for 1 hr. The reaction was quenched with aq. ammonium chloride. Mixture was warmed to room temperature then diluted with water. The mixture was extracted 2 times with ethyl acetate and the aqueous phase was discarded. The material was dried (magnesium sulfate), filtered, and concentrated to dryness. Silica gel chromatography gave the title compound as white foam in 81% yield. MS m/e (M-C$_4$H$_8$O$_2$+H)+=381.2.

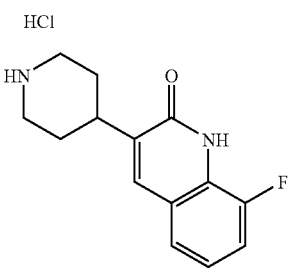

Intermediate 8

8-Fluoro-3-(piperidin-4-yl)quinolin-2(1H)-one hydrochloride. tert-Butyl 4-(1-(3-fluoro-2-pivalamidophenyl)-1-hydroxy-3-methoxy-3-oxopropan-2-yl)piperidine-1-carboxylate (16.4 mmol, 7.86 g) was dissolved in methanol (20 mL). Water (45 mL) was added to the mixture followed by concentrated hydrochloric acid (183 mmol, 15 mL). Reaction was heated to reflux and held for 2.5 hours. Reaction mixture was concentrated in vacuo. Residue was dissolved in ethanol (50 mL) then concentrated in vacuo. Residue was crystallized from ethanol. Solids were filtered off, washed with cold ethanol then dried in vacuo. Title compound was obtained as white solid in 83% yield. $^1$H NMR (500 MHz, DMSO-$d_6$): δ=11.85 (s, 1H), 8.98 (m, 1H), 8.85 (m, 1H), 7.75 (s, 1H), 7.54 (d, J=7.63, 1H), 7.36 (dd, J1=10.22, J2=8.09, 1H), 7.21-7.11 (m, 1H), 3.41-3.29 (m, 2H), 3.14-2.94 (m, 3H), 2.02 (d, J=13.43, 2H), 1.88-1.71 (m, 2H). MS m/e (M+H)$^+$=247.2.

Intermediate 9

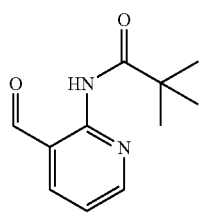

N-(3-Formylpyridin-2-yl)pivalamide. Triethlyamine (7.6 mL, 54 mmol), was added to a solution of 2-aminopyridine-3-carboxaldehyde (4.45 g, 36 mmol) in dichloromethane (70 mL). Mixture was cooled to 0° C. A solution of pivaloyl chloride (5.3 mL, 43 mmol) in dichloromethane (30 mL) was added to the mixture. Reaction was warmed to room temperature. Mixture stirred at room temperature for 63 hours. Mixture was washed successively with water (2×50 mL) and brine (30 mL). Organic layer was dried (magnesium sulfate), filtered and concentrated in vacuo. Silica gel chromatography afforded the title compound as off-white solid in 90% yield. (M+H)$^+$=207.1.

Intermediate 10

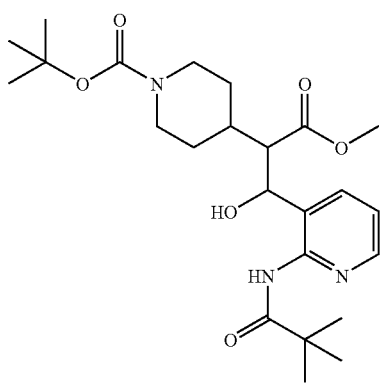

tert-Butyl 4-(1-hydroxy-3-methoxy-3-oxo-1-(2-pivalamidopyridin-3-yl)propan-2-yl)piperidine-1-carboxylate. A solution of diisopropylamine (6.0 mL, 43 mmol) in tetrahydrofuran (200 mL) was cooled to −78° C. A 2.5M solution of n-butyllithium in hexanes (17.0 mL, 43 mmol) was added to the mixture drop-wise. Mixture was held at −78° C. with stirring for 20 minutes. A solution of tert-butyl 4-(2-methoxy-2-oxoethyl)piperidine-1-carboxylate (9.3g, 36 mmol) in tetrahydrofuran (35 mL) was added to the mixture drop-wise. Mixture was held at −78° C. for 1.5 hours. In a separate flask, 60% sodium hydride in mineral oil (1.57 g, 39 mmol) was washed in hexanes and then suspended in tetrahydrofuran (70 mL). Mixture was cooled to 0° C. A solution of N-(3-formylpyridin-2-yl)pivalamide (6.74 g, 33 mmol) in tetrahydrofuran (20 mL) was added to the mixture drop-wise. Reaction was held at 0° C. with stirring for 2 hours. Mixture was warmed to room temperature and then added to the butyllithium containing solution drop-wise. Reaction mixture was held at −78° C. with stirring for 2 hours. Mixture was allowed to slowly warm to room temperature. Mixture stirred at room temperature for 14 hours. Reaction was quenched with aqueous ammonium chloride. The mixture was extracted with ethyl acetate (2×100 mL). Organic extracts were combined, dried (magnesium sulfate), filtered and concentrated in vacuo. Silica gel chromatography afforded the title compound as white foam in 93% yield. (M+H)$^+$=464.2.

Intermediate 11

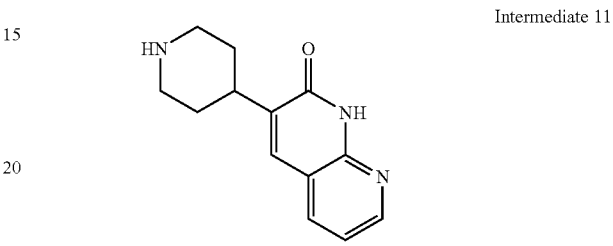

3-(Piperidin-4-yl)-1,8-naphthyridin-2(1H)-one dihydrochloride. Concentrated hydrochloric acid (25 mL, 305 mmol) was added with stirring to a mixture of tert-butyl 4-(1-hydroxy-3-methoxy-3-oxo-1-(2-pivalamidopyridin-3-yl)propan-2-yl)piperidine-1-carboxylate (14.0 g, 30.2 mmol) and water (75 mL). Reaction was heated to reflux and held for 25 hours. Mixture was concentrated in vacuo. Residue was crystallized from ethanol. Title compound was obtained as white solid in 33% yield. (M+H)$^+$=230.2.

Intermediate 12

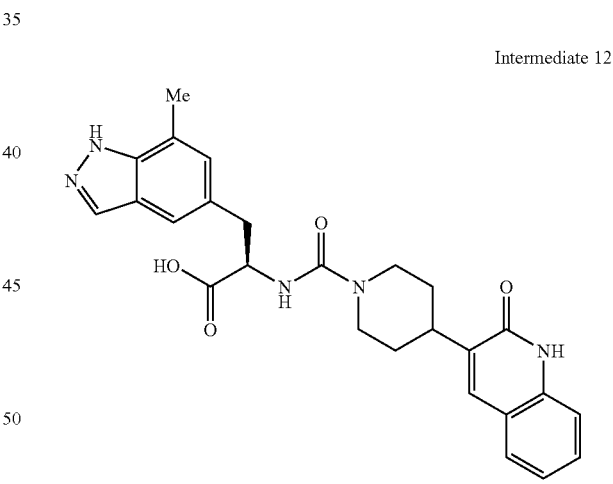

(R)-3-(7-methyl-1H-indazol-5-yl)-2-(4-(2-oxo-1,2-dihydroquinolin-3-yl)piperidine-1-carboxamido)propanoic acid. To a solution of (R)-methyl 2-(benzyloxycarbonyl)-3-(7-methyl-1H-indazol-5-yl)propanoate (10.0 g, 27 mmol) in methanol (125 mL) under nitrogen was added 10% Pd on Carbon (2.0 g). Hydrogen atmosphere was introduced to the reaction mixture and hydrogenolysis was conducted in a Parr shaker at 50 psi for 3 h. At the end of the reaction, the catalyst was filtered, added 2.0 M solution of hydrogen chloride in ether (15 mL) and the solvent was evaporated. The resulting white solid was washed with dry ether to provide (R)-methyl 2-amino-3-(7-methyl-1H-indazol-5-yl)propanoate hydrochloride in 90% yield.

To a solution of (R)-methyl 2-amino-3-(7-methyl-1H-indazol-5-yl)propanoate hydrochloride (2.69 g, 10 mmol) in DMF (20 mL) was added N,N'-disuccinimidyl carbonate followed by triethylamine (5.6 mL, 40 mmol). After 20 min, 3-(piperidin-4-yl)quinolin-2(1H)-one (2.28 g, 10 mmol) was added at once. The reaction mixture was stirred at room temperature for 12 h. The reaction mixture was then diluted with CH$_2$Cl$_2$ (250 mL), washed with water (2×100 mL), 1 M sodium hydroxide (30 mL) and then with 1.0 M hydrogen chloride (100 mL). The organic phase was dried (Na$_2$SO$_4$) and then purified by flash chromatography using 5% methanol in dichloromethane to give (R)-methyl 3-(7-methyl-1H-indazol-5-yl)-2-(4-(2-oxo-1,2-dihydroquinolin-3-yl)piperidine-1-carboxamido)propanoate in 68% yield. MS (ESI) 488 (M+H) ; R$_f$=2.14.

To a solution of (R)-methyl 3-(7-methyl-1H-indazol-5-yl)-2-(4-(2-oxo-1,2-dihydroquinolin-3-yl)piperidine-1-carboxamido)propanoate (2.44 g, 5 mmol) in THF (50 mL) was added a solution of lithium hydroxide (420 mg, 10 mmol) in water (15 mL) at room temperature. After 1 h, most of the THF was removed and neutralized with 1.0 M hydrogen chloride to give (R)-3-(7-methyl-1H-indazol-5-yl)-2-(4-(2-oxo-1,2-dihydroquinolin-3-yl)piperidine-1-carboxamido) propanoic acid as a white solid in 95% yield. $^1$H-NMR (CD$_3$OD) δ 7.97 (s, 1H), 7.66 (d, J=8 Hz, 1H), 7.60 (s, 1H), 7.51-7.48 (m, 2H), 7.33 (d, J=8 Hz, 1H), 7.27-7.24 (m, 1H), 7.12 (s, 1H), 4.61-4.58 (m, 1H), 4.14-4.08 (m, 2H), 3.76-3.73 (m, 2H), 3.13-2.84 (m, 4H), 2.54 (s, 3H), 1.90-1.84 (m, 4H), 1.48-1.34 (m, 2H); MS (ESI) 474 (M+H) ; R$_f$=1.89.

Intermediate 13

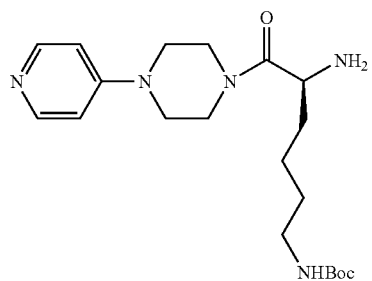

(S)-tert-butyl 5-amino-6-oxo-6-(4-(pyridin-4-yl)piperazin-1-yl)hexylcarbamate. To a solution of (S)-2-(benzyloxycarbonyl)-6-(tert-butoxycarbonyl)hexanoic acid (3.99 g, 10.5 mmol) in dichloromethane was added 1-(pyridin-4-yl)piperazine (1.63 g, 10 mmol) followed by 2-(1H-benzotriazole-1-yl)-1,1,3,3-tetramethyluronium tetrafluoroborate (3.37 g, 10.5 mmol) and triethylamine (4.0 mL) at room temperature. After stirring for 4 h, the reaction mixture was diluted with dichloromethane (200 mL), washed with aqueous sodium hydrogencarbonate, 1.0 M sodium hydroxide. The crude product was purified by flash chromatography using 5% methanol in dichloromethane containing 1% of aqueous ammonium hydroxide to give 5.0 g of coupled product. To the coupled product (5.0 g) in methanol (75 mL) was added 10% Pd on carbon (300 mg) under nitrogen. Hydrogen was introduced and hydrogenolysis was carried out at 50 psi for 2 h. The catalyst was filtered and the solvent was removed to give (S)-tert-butyl 5-amino-6-oxo-6-(4-(pyridin-4-yl)piperazin-1-yl)hexylcarbamate in 95% yield as a white solid. $^1$H-NMR (CD$_3$OD) δ 8.31 (m, 2H), 7.35 (s, 2H), 6.67 (m, 2H), 4.55 (m, 1H), 3.69-3.66 (m, 4H), 3.40-3.37 (m, 4H), 3.12-3.05 (m, 2H), 2.15-1.95 (m, 4H), 1.62-1.44 (m, 4H), 1.42 (s, 9H); MS (ESI) 392 (M+H) ; R$_f$=0.99.

Intermediate 15

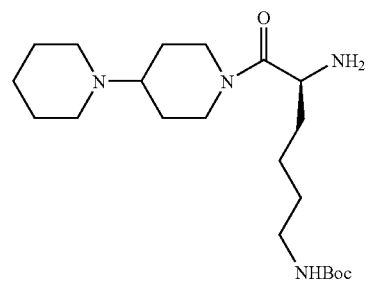

(S)-tert-butyl 5-amino-6-oxo-6-(4-(piperidin-1-yl)piperidin-1-yl)hexylcarbamate. (S)-tert-butyl 5-amino-6-oxo-6-(4-(pyridin-4-yl)piperazin-1-yl)hexylcarbamate was prepared from 4-(piperidin-1-yl)piperidine and (S)-2-(benzyloxycarbonyl)-6-(tert-butoxycarbonyl)hexanoic acid using the same procedure as described for (S)-tert-butyl 5-amino-6-oxo-6-(4-(pyridin-4-yl)piperazin-1-yl)hexylcarbamate in 89% yield. MS (ESI) 397 (M+H) ; R$_f$=1.01.

Intermediate 16

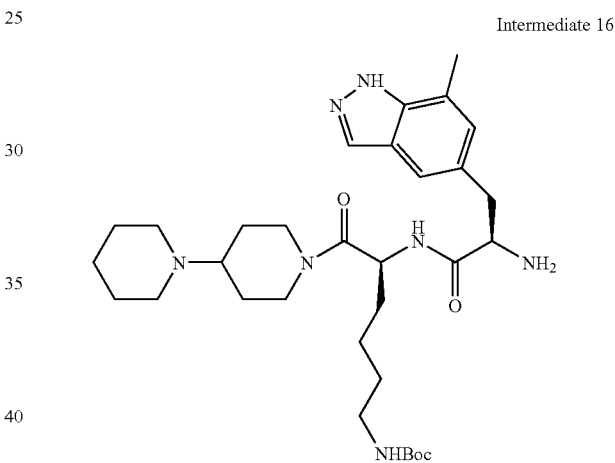

tert-Butyl (S)-5-((R)-2-amino-3-(7-methyl-1H-indazol-5-yl)propanamido)-6-oxo-6-(4-(piperidin-1-yl)piperidin-1-yl)hexylcarbamate. To a solution of (S)-tert-butyl 5-amino-6-oxo-6-(4-(pyridin-4-yl)piperazin-1-yl)hexylcarbamate (1.23 g, 3.1 mmol) in dichloromethane (75 mL) was added (R)-2-(benzyloxycarbonyl)-3-(7-methyl-1H-indazol-5-yl)propanoic acid (1.06 g, 3 mmol) followed by 2-(1H-benzotriazole-1-yl)-1,1,3,3-tetramethyluronium tetrafluoroborate (1.03 g, 3.2 mmol) and triethylamine (2.0 mL). After 1 h, the reaction mixture was washed with 1.0 M sodium hydroxide followed by brine. The solvent was removed and the crude product was purified by flash chromatography using 5% methanol in dichloromethane containing 2% aqueous ammonium hydroxide (ammonia content 28-30%) to give the coupled product in 95% yield. MS (ESI) 732 (M+H) ; R$_f$=2.16.

The above coupled product was dissolved in methanol (50 mL) and added 10% Pd on carbon (150 mg) under nitrogen. Hydrogen was introduced at 55 psi and hydrogenolysis was carried out for 2 h. The catalyst was filtered and removed the solvent to give tert-Butyl (S)-5-((R)-2-amino-3-(7-methyl-1H-indazol-5-yl)propanamido)-6-oxo-6-(4-(piperidin-1-yl) piperidin-1-yl)hexylcarbamate in 95% yield. $^1$H-NMR (CD$_3$OD) δ 7.99 (s, 1H), 7.7.41 (m, 1H), 7.09 (m, 1H), 4.76-

4.69 (m, 1H), 4.61-4.50 (m, 1H), 3.65-3.63 (m, 1H), 3.10-2.80 (m, 5H), 2.60-2.48 (m, 4H), 2.56 (s, 3H), 2.05-1.85 (m, 2H), 1.62-0.90 (m, 16H), 1.49 (s, 9 H); MS (ESI) 598 (M+H); $R_f$=1.41.

Intermediate 17

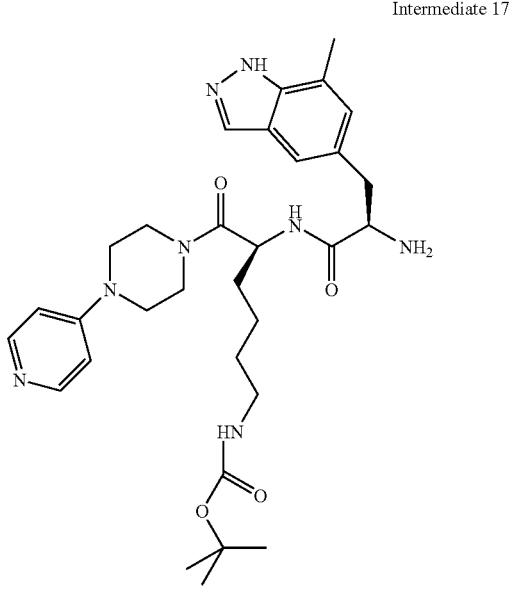

tert-butyl (S)-5-((R)-2-amino-3-(7-methyl-1H-indazol-5-yl)propanamido)-6-oxo-6-(4-(pyridin-4-yl)piperazin-1-yl) hexylcarbamate. The title compound was prepared from (R)-2-(benzyloxycarbonyl)-3-(7-methyl-1H-indazol-5-yl) propanoic acid and (S)-tert-butyl 5-amino-6-oxo-6-(4-(pyridin-4-yl)piperazin-1-yl)hexylcarbamate using the same procedure as described for give tert-Butyl (S)-5-((R)-2-amino-3-(7-methyl-1H-indazol-5-yl)propanamido)-6-oxo-6-(4-(piperidin-1-yl)piperidin-1-yl)hexylcarbamate. The product was obtained in 86% overall yield. $^1$H-NMR (CD$_3$OD) δ 8.15 (d, J=6 Hz, 2H), 7.98 (s, 1H), 7.41 (s, 1H), 7.08 (s, 1H), 6.83 (d, J=6 Hz, 2H), 4.72-4.65 (m, 1H), 3.81-3.56 (m, 4H), 3.52-3.30 (m, 4H), 3.08-2.71 (m, 5H), 2.55 (s, 3H), 1.60-0.95 (m, 6H), 1.42 (s, 9H); MS (ESI) 593 (M+H) ; $R_f$=1.42.

Intermediate 18

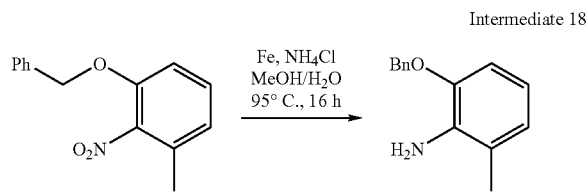

2-(Benzyloxy)-6-methylbenzenamine. To the clear solution of the nitro compound (15.0 g, 61.6 mmol) in MeOH (300 mL), was added H$_2$O (250 mL) and a white suspension was formed. Fe (10.3 g, 185 mmol, 3 equiv) and NH$_4$Cl (16.5 g, 308 mmol, 5 equiv) were added and the resulting suspension was heated at 95° C. for 16 h. The reaction mixture was filtered through a pad of celite while it was still hot, and the filter cake was rinsed with MeOH (350 mL). MeOH was removed completely from the filtrate. The aqueous residue was made basic by the addition of 1N NaOH and saturated with NaCl, then it was extracted wit EtOAc twice. The organic layers were combined and dried over Na$_2$SO$_4$. After filtration, the solvents were removed and the residue was subjected to flash chromatograph (SiO$_2$) using EtOAc/hexanes (1:9) as eluent to afford the title compound as a white solid (11.4 g, 87% yield). $^1$HNMR (CDCl$_3$, 500 MHz) δ 7.46-7.43 (m, 2H), 7.41-7.38 (m, 2H), 7.35-7.32 (m, 1H), 6.78-6.73 (m, 2H), 6.65 (t, J=7.6 Hz, 1H), 5.09 (s, 2H), 3.80 (br s, 2H), 2.20 (s, 3H); $^{13}$CNMR (CDCl$_3$, 125 MHz) δ 146.3, 137.4, 134.7, 128.7, 128.0, 127.7, 123.1, 122.9, 117.6, 109.8, 70.6, 17.4; Mass Spec. 214.16 (MH$^+$), Calc. for C$_{14}$H$_{15}$NO 213.12.

Intermediate 19

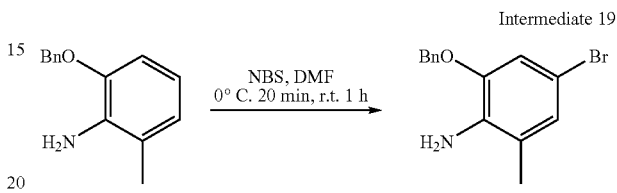

2-(Benzyloxy)-4-bromo-6-methylbenzenamine. To a flame dried round bottom flask, was added the aniline (6.82 g, 32 mmol) and DMF (10 ml). The resulting clear solution was cooled to ° C. for 5 min and NBS (5.70 g, 32 mmol, 1 equiv) was added at once. The resulting mixture was stirred at ° C. for 20 min and at r.t. for 1 h. DMF was removed under high vacuum and the residue was subjected to flash chromatography (SiO$_2$) using EtOAc/hexanes (1:9) as effluent to afford the title compound as tannish orange solid (7.05 g, 75% yield). $^1$HNMR (CDCl$_3$, 500 MHz) δ 7.46-7.36 (m, 5H), 6.92 (s, 1H), 6.90 (s, 1H), 5.04 (s, 2H), 3.79 (br s, 2H), 2.16 (s, 3H); $^{13}$CNMR (CDCl$_3$, 125 MHz) δ 146.8, 136.8, 133.9, 128.8, 128.4, 127.8, 125.6, 124.2, 113.1, 109.0, 70.9, 17.2; Mass Spec. 294.31 (MH$^+$), Calc. for C$_{14}$H$_{14}$BrNO 291.03.

Intermediate 20

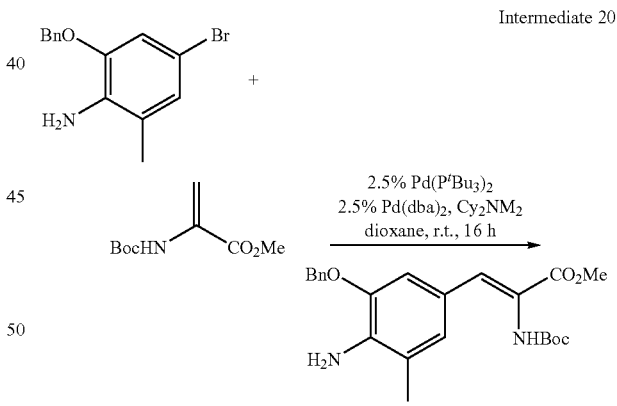

(Z)-Methyl 3-(4-amino-3-(benzyloxy)-5-methylphenyl)-2-(tert-butoxycarbonyl)acrylate. To a flame dried 500 mL of Schlenck flask, was added Pd(P$^t$Bu$_3$)$_2$ (308 mg, 0.60 mmol, 0.025 equiv) and Pd(dba)$_2$ (346 mg, 0.60 mmol, 0.025 equiv), it was degassed and purged with N$_2$ 5 times. The dioxane (53 mL) solution of the bromide (7.05 g, 24.1 mmol, 1 equiv), the enamide (5.33 g, 26.5 mmol, 1.1 equiv) and Cy$_2$NMe (5.61 mL, 26.5 mmol, 1.1 equiv), after it was degassed by a flow of N$_2$ for 45 min, was cannulated into the Schlenck flask. The resulting mixture was degassed and purged with N$_2$ 5 times and it was stirred at r.t. for 16 h. The mixture was diluted with EtOAc (500 mL) and filtered through a pad of SiO$_2$ and rinsed with EtOAc (300 mL). Solvents were removed and the residue was subjected to flash chromatography (SiO$_2$) using EtOAc/hexanes (1:3 and 1:2) as eluent to afford the title compound as an orange solid (8.04 g, 81% yield). The orange solid was recrystalized using MeOH (110 mL) and acetone (20 mL), a tan solid (5.65 g, 57% yield) was obtained, which was used directly for the asymmetric hydrogenation reaction. Solvents were removed from the mother liquor and the residue was subjected to flash chromatography (SiO$_2$) using EtOAc/hexanes (1:3 and 1:2) as eluent to afford an orange solid (2.40 g, 24% yield). For the recrystalized product: $^1$HNMR (CDCl$_3$, 500 MHz) δ 7.44-7.37 (m, 4H), 7.35-7.32 (m, 1H), 7.12 (d, J=1.0 Hz, 1H), 6.99 (d, J=1.0 Hz, 1H), 6.08 (br s 1H), 5.06 (s, 2H), 4.08 (br s, 2H), 3.81 (s, 3H), 2.16 (s, 3H), 1.45 (br s, 9H); $^{13}$CNMR (CDCl$_3$, 125 MHz) δ 166.7, 145.4, 137.0, 136.9, 133.6, 128.7, 128.2, 127.8, 126.8, 123.0, 121.7, 111.3, 80.6, 70.6, 52.4, 28.4, 17.3; Mass Spec. 413.23 (MH$^+$), Calc. for C$_{23}$H$_{28}$N$_2$O$_5$ 412.20

Intermediate 21

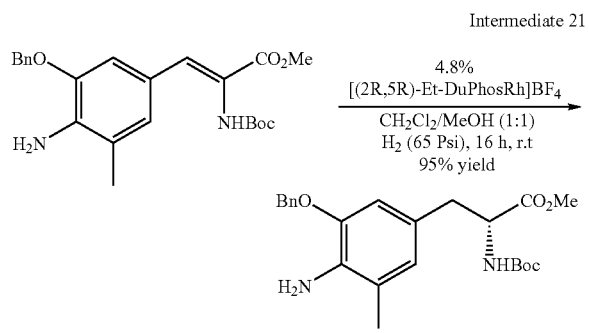

(R)-Methyl 3-(4-amino-3-(benzyloxy)-5-methylphenyl)-2-(tert-butoxycarbonyl)propanoate. The enamide (5.60 g, 13.6 mmol) was weighed into a flame-dried 500 mL of hydrogenation bottle, followed by the addition of CH$_2$Cl$_2$ (50 mL) and MeOH (50 mL). The bottle was swirled to form a light brown suspension, and this suspension was degassed by a flow of N$_2$ for 30 min. The sealed bottle was brought to a Parr Hydrogenator. As soon as (−)-1,2-bis((2R,5R)-2,5-diethylphospholano)bezene(cyclooctadiene)rhodium(I) tetrafluoroborate ([(2R,5R)-Et-DuPhosRh]BF$_4$) (430 mg, 0.65 mmol) was added, the bottle was put onto a Parr Hydrogenator. After 5 cycles of purging of H$_2$ (60 psi) and vacuuming, the final H$_2$ pressure was set at 65 psi and the suspension was agitated at r.t. for 16 h. Solvents were removed and the residue was subjected to flash chromatography (SiO$_2$) using EtOAc/hexanes (1:3) as eluent to afford the title compound as an off-white solid (5.31 g, 95% yield). $^1$HNMR (CDCl$_3$, 500 MHz) δ 7.44-7.37 (m, 4H), 7.35-7.32 (m, 1H), 6.52 (s, 1H), 6.48 (s, 1H), 5.03 (d, J=1.8 Hz, 2H), 4.94-4.92 (m, 1H), 4.50-4.48 (m, 1H), 3.73 (s, 2H), 3.67 (s, 3H), 2.96-2.94 (m, 2H), 2.14 (s, 3H), 1.43 (s, 9H); 13CNMR (CDCl$_3$, 125 MHz) δ 172.7, 155.3, 146.3, 137.2, 133.6, 128.7, 128.1, 127.7, 124.9, 124.0, 122.8, 110.7, 79.9, 70.7, 54.8, 52.2, 37.9, 28.4, 17.4; Mass Spec. 415.30 (MH$^+$), Calc. for C$_{23}$H$_{30}$N$_2$O$_5$ 414.22.

Intermediate 22

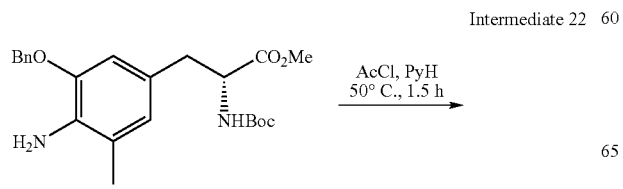

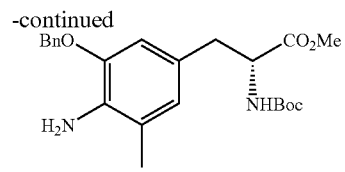

(R)-Methyl 3-(4-acetamido-3-(benzyloxy)-5-methylphenyl)-2-(tert-butoxycarbonyl)propanoate. To the mixture of the aniline (2.0 g, 4.83 mmol) in pyridine (50 mL) at 50° C., was added AcCl (0.52 mL, 7.25 mL, 1.5 equiv). It was kept at 50° C. for 1 h, the second portion of AcCl (0.52 mL, 7.25 mL, 1.5 equiv) was added, after 20 min the third portion of AcCl (0.52 mL, 7.25 mL, 1.5 equiv) was added. The mixture was kept at 50° C. for 1.5 h. All solvents were removed in vacuum and the residue was extracted with EtOAc and sat. aq. NaHCO$_3$. The organic layers were combined and dried over Na$_2$SO$_4$. After filtration, all volatiles were removed. The solid was dissolved in 2MNH$_3$-MeOH/CH$_2$Cl$_2$ (1:9) and vaporized. This process was repeated three times to remove residual pyridine. The title compound was obtained a white solid (2.25 g). $^1$HNMR (CDCl$_3$, 500 MHz) δ 7.38-7.36 (m, 4H), 7.34-7.32 (m, 1H), 6.80 (s, 0.78H), 6.65-6.58 (m, 2.03H), 6.46 (S, 0.18H), 5.00 (s, 2H), 5.04-4.96 (m, 1H), 4.55 (br s, 1H), 3.67 (s, 3), 3.03-2.98 (m, 2H), 2.11 (s, 3H), 2.14 (s, 2.2H), 1.77 (s, 0.5H), 1.64 (s, 0.3H), 1.42 (s, 9H); Mass Spec. 457.61 (MH$^+$), Calc. for C$_{25}$H$_{32}$N$_2$O$_6$ 456.23.

Intermediate 23

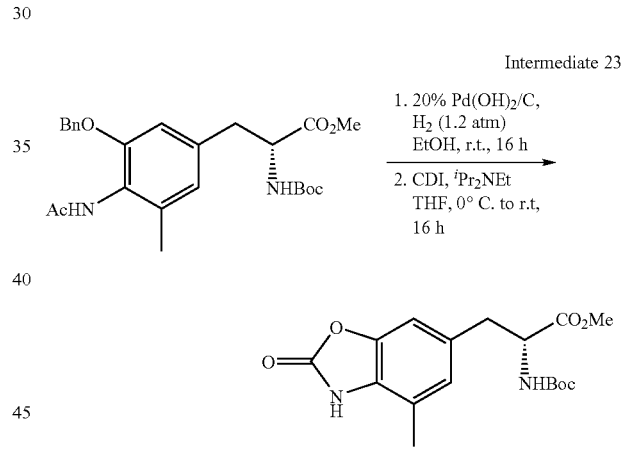

(R)-Methyl 2-(tert-butoxycarbonyl)-3-(4-methyl-2-oxo-2,3-dihydrobenzo[d]oxazol-6-yl)propanoate. To a flame dried hydrogenation bottle, was added the amide (2.20 g, 4.82 mmol) and EtOH (120 mL). The clear solution was degassed by a flow of N2 10 min, and 20% Pd(OH)$_2$/C (0.88 g) was added. It was hydrogenated at 1.2 atm of H$_2$ for 16 h. The mixture was vacuumed and purged with N$_2$, filtered through a pad of celite. Solvents were removed to afford the phenol as an off-white solid. The phenol was dissolved in THF (100 mL) at 0° C., followed by the addition of CDI (1.56 g, 9.64 mmol, 2 equiv) and $^i$Pr$_2$NEt (1.7 mL, 9.64 mmol, 2 equiv). The mixture was then stirred at 0° C. for 2 h and at r.t for 16 h. All solvents were removed and the residue was subjected flash chromatography (SiO$_2$) using EtOAc/hexanes (2:3) as eluent to afford the title compound as an off-white solid (1.69 g, 83% yield). $^1$HNMR (CDCl$_3$, 500 MHz) δ 9.70 (s, 1H), 6.82 (s, 1H), 6.73 (s, 1H), 5.11-5.09 (m, 1H), 4.57-4.55 (m, 1H), 3.74 (s, 3H), 3.13-3.09 (m, 1H), 3.03-2.99 (m, 1H), 2.29 (s, 3H), 1.42 (s, 9H); $^{13}$CNMR (CDCl$_3$, 125 MHz) δ 172.6, 156.5, 155.3, 143.8, 130.7, 127.8, 126.4, 120.2, 108.4, 80.2, 54.8, 52.5, 38.4, 28.4, 16.2; Mass Spec. 723.59 (MH$^+$), Calc. for C$_{34}$H$_{44}$N$_4$NaO$_{12}$ [2M+Na] 723.29.

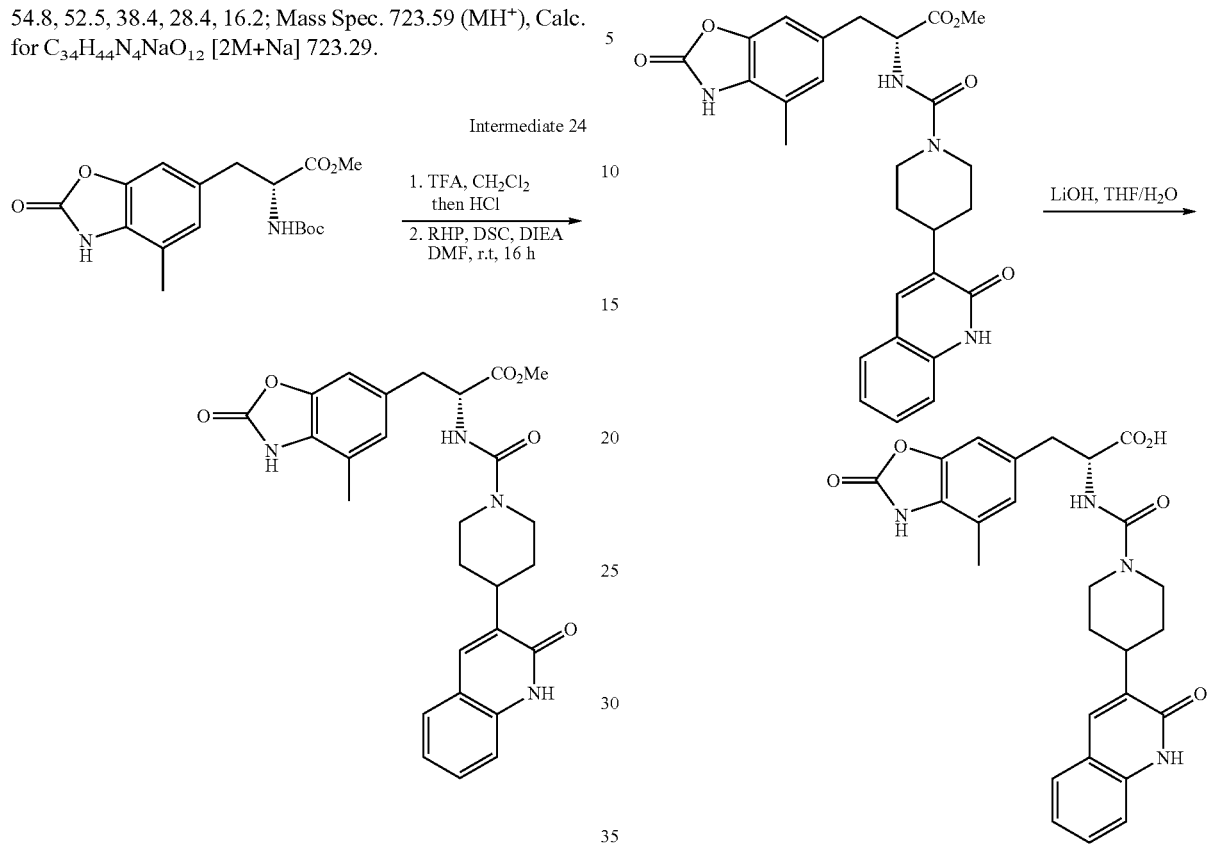

Intermediate 24

Intermediate 25

(R)-Methyl 3-(4-methyl-2-oxo-2,3-dihydrobenzo[d]oxazol-6-yl)-2-(4-(2-oxo-1,2-dihydroquinolin-3-yl)piperidine-1-carboxamido)propanoate. To a clear solution of the Boc amino ester (690 mg, 1.97 mmol) in CH$_2$Cl$_2$ (8.0 mL) at 0° C., was added TFA (2.0 mL). The mixture was stirred at 0° C. for 1 h. All volatiles were removed and the residue was dissolved in CH$_2$Cl$_2$ (10 mL) and 2N HCl in ether (1.2 mL, 2.4 mmol) was added to form a white suspension. All volatiles were removed under high vacuum. The resulting white solid was dissolved in DMF (15 mL), followed by the addition of $^i$Pr$_2$NEt (1.7 mL, 9.85 mmol, 5 equiv), and DSC (504 mg, 1.97 mmol, 1 equiv). The mixture was stirred at r.t. for 1 h, and 3-(piperidin-4-yl)quinolin-2(1H)-one (477 mg, 2.09 mmol, 1.06 equiv) was added and the resulting mixture was stirred at r.t. for 16 h. All volatiles were removed and the residue was subjected to flash chromatography (SiO$_2$) using 2M NH$_3$-MeOH/CH$_2$Cl$_2$ (1:20) as eluent to afford the title compound as an off-white solid (0.97 g, 98% yield). $^1$H NMR (CDCl$_3$, 500 MHz) δ 11.48 (br s, 1H), 8.00 (br s, 1H), 7.52-7.50 (m, 2H), 7.41 (t, J=7.9 Hz, 1H), 7.31 (d, J=8.2Hz, 1H), 7.15 (t, J=7.6 Hz, 1H), 6.80 (s, 1H), 6.72 (s, 1H), 5.35-5.33 (m, 1H), 4.81-4.77 (m 1H), 4.11-4.05 (m, 2H), 3.73 (s, 3H), 3.14-3.04 (m, 4H), 2.96-2.88 (m 1H), 2.52 (br s, 1H), 2.26 (s, 3H), 2.14 (s, 2H), 196-1.93 (m, 2H), 1.53-1.49 (m, 2H); Mass Spec. 505.61 (MH$^+$), Calc. for C$_{27}$H$_{28}$N$_4$O$_6$ 504.20.

(R)-3-(4-Methyl-2-oxo-2,3-dihydrobenzo[d]oxazol-6-yl)-2-(4-(2-oxo-1,2-dihydroquinolin-3-yl)piperidine-1-carboxamido)propanoic acid. The solution of LiOH.H$_2$O (320 mg, 7.6 mmol, 4 equiv) in H$_2$O (10 mL) was added at 0° C. to the solution of the ester (960 mg, 1.90 mmol, 1 equiv) in THF (27 mL). The resulting clear solution was stirred at 0° C. for 3 h. All THF was removed and the pH was adjusted to 2. The resulting white precipitate was stirred at 0° C. for 1 h and filtered. The solid was dried under high vacuum to afford the acid as an off-white solid (840mg, 90% yield). Mass Spec. 491.19 (MH+), Calc. for C$_{26}$H$_{26}$N$_4$O$_6$ 490.19.

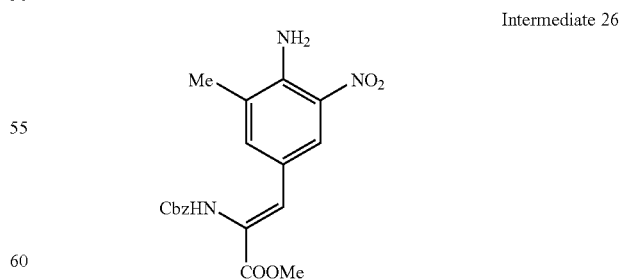

Intermediate 26

(Z)-Mehtyl-3-(4-amino-3-methyl-5-nitrophenyl)-2-(benyloxycarbonyl)acrylate. 4-iodo-2-methyl-6-nitrobenzenamine.HCl (6.28 g, 20 mmol) and tetrabutylammonium chloride (6.67g, 24 mmol)was dissolved in DMF(30-40 mL) which was degassed for 10 min, followed by the addition of methyl 2-(benzyloxycarbonyl)acrylate (5.65 g, 24 mmol) and Pd(OAc)$_2$ (0.674 g, 3 mmol), and triethylamine (8.0 mL, 57 mmol) under N$_2$. The mixture was heated at 70° C. for 2.5 hours (the reaction was monitored by LC-MS and TLC, ethyl acetate/hexanes=1:1, R$_f$=0.24). All volatiles were removed, and the residue was dissolved in CHCl$_3$, which was washed with brine twice, and the organic layer was dried over MgSO$_4$. After filtration, solvents were removed in vacuo and the residue was subjected to flash chromatography using EtOAc/hexanes (1:4, 1:2, 1:1) as eluent to give the title compound as an orange solid 6.87g (71%, yield). All of these solids were refluxed in ethyl acetate (125 mL) and the resulting dark brown solution was filtered. The filtrate was cooled down to r.t. and stored in refrigerator (4° C.) for 2 hrs, then filtered to afford the title compound in a very pure form as an orange solid (5.26 g, recovery yield 62%). $^1$HNMR (CDCl$_3$, 500 MHz) δ 8.23 (s, 1H), 7.47 (s, 1H), 7.33 (br s, 5H), 7.28 (s, 1H), 6.36 (v br s, 3H), 5.12 (s, 2H), 3.82 (s, 3H), 2.14 (s, 3H); Mass Spec. 386.14 (MH$^+$), Calc. for C$_{19}$H$_{19}$N$_3$O$_6$ 385.13.

Intermediate 27

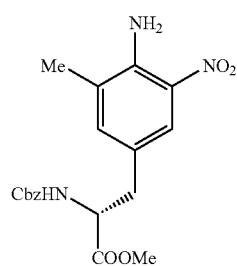

(R)-Methyl 3-(4-amino-3-methyl-5-nitrophenyl)-2-(benzyloxycarbonyl)propanoate. In a glove bag that was subjected to three vacuum/nitrogen purge cycles, an AIRFREE® (Schlenk) reaction flask equipped with stir bar was charged with (−)-1,2-bis((2R,5R)-2,5-diethylphospholano)benzene (cyclooctadiene)rhodium (I) trifluoromethylsulfonate ([(2R, 5R)_Et-DuPhosRh]BF4)(537 mg, 0.8 mmol). This flask was sealed with a rubber septum, and removed from the glove bag. The eanamide (1.84 g, 4.78 mmol) was weighed into a second AIRFREE® (Schlenk) reaction flask equipped with stir bar and sealed with a rubber septum. After three vacuum/nitrogen purge cycles, a degassed (by a flow of N2 for 45 min) mixture of anhydrous CH$_2$Cl$_2$/MeOH (1:1, 150 mL) was added. The resulting solution was again subjected to three vacuum/nitrogen purge cycles, then it was cannulated into the AIRFREE® (Schlenk) reaction flask containing the catalyst. The reaction mixture was subjected to five vacuum/H2 purge cycles before opening the flask to 1 atmosphere H$_2$ (balloon). After 3 h, the mixture was vacuumed and purged with N2 five times. All solvents were removed and the residue was subjected to flash chromatography (EtOAc/hexanes=1:1) to give the compound as a yellow solid (1.5 g, 82% yield). $^1$HNMR (DMSO-d$_6$, 500 MHz) δ 7.84 (d, J=8.2 Hz, 1H), 7.80 (s, 1H), 7.35-7.24 (m, 6H), 7.11 (br s, 2H), 5.02-4.96 (m, 2H), 4.26-4.21 (m, 1H), 3.65 (s, 3H), 2.97-2.92 (m, 1H), 2.78-2.73 (m, 1H), 2.19 (s, 3H); Mass Spec. 388.10 (MH$^+$), Calc. for C$_{19}$H$_{21}$N$_3$O$_6$ 387.14.

Intermediate 28

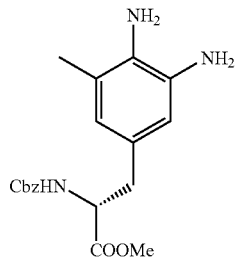

(R)-Methyl-2-(benzyloxycarbonyl)-3-(3,4-diamino-5-methylphenyl)propanoate. Under vigorous stirring, a solution of the nitro compound (4.82 g, 12.45 mmol) in MeOH (90 mL) was added to the mixture of NH$_4$Cl (6.67 g, 124.5 mmol) and Fe powder (4.17 g, 74.7 mmol) in H$_2$O/MeOH (70 mL/50 mL). The mixture was heated at 85° C. for 1 h. The reaction mixture was filtered through a pad of celite while it was still hot, washed thoroughly with MeOH. All solvents were removed and the resulting solids were azotropically dried with anhydrous EtOH to afford the title compound as brownish orange solid which was used for the next step immediately [the product was prone to oxidation, the longer it was stored in the refrigerator (even under N$_2$ atmosphere), the lower the yield for the next step it will be]. Mass Spec. 358.13 (MH$^+$), Calc. for C$_{19}$H$_{23}$N$_3$O$_4$ 357.17.

Intermediate 29

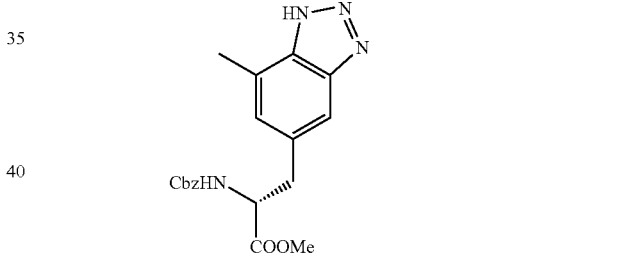

(R)-Methyl-2-(benzyloxycarbonyl)-3-(7-methyl-1H-benzo[d][1, 2, 3]triazol-5-yl)propanoate. To the suspension of the diamine (12.45 mmol) in HOAc/H$_2$O (97 mL/150 mL), a solution of sodium nitrite (859 mg, 12.45 mmol in 15 mL of H$_2$O) was added dropwise at room temperature. The reaction mixture was stirred at the same temperature for 35 min. All volatiles were removed in vacuum, and the residue was treated with a mixture of ethyl acetate/H$_2$O. After separation, the aqueous layer was extracted with ethyl acetate twice, and combined ethyl acetate extracts were washed once with brine and dried over MgSO$_4$. After filtration, all solvents were removed and the residue was subjected to flash chromatography using EtOAc/hexanes (2:3) as eluent to afford the title compound as a light tan solid (4.03 g, 85% yield for two steps). $^1$HNMR (CDCl$_3$, 500 MHz) δ 7.36 (s, 1H), 7.31-7.21 (m, 5H), 6.97 (s, 1H), 5.40-5.38 (m, 1H), 5.12-5.04 (m, 2H), 4.73-4.71 (m, 1H), 3.74 (s, 3H), 3.31-3.27 (m, 1H), 3.19-3.14 (m, 1H), 2.64 (s, 3H); Mass Spec. 369.16 (MH$^+$), Calc. for C$_{19}$H$_{20}$N$_4$O$_4$ 368.15.

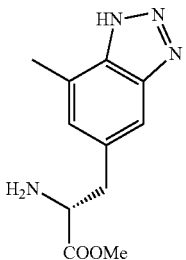

Intermediate 30

(R)-Methyl-2-amino-3-(7-methyl-1H-benzo[d][1,2,3]triazol-5-yl)propanoate hydrochloride. N-Boc ester (2.2g, 6.0 mmol) was dissolved in 4.4% HCOOH in MeOH (freshly prepared, 40 mL), followed by the addition of 10% Pd/C 1.1 g) under $N_2$. The reaction mixture was stirring at room temperature overnight and it was filtered through a pad of celite and washed thoroughly with MeOH. To the filtrate, 2 mL of 4N HCl in dioxane was added and the mixture was concentrated to dryness to yield the title compound as a light tan solid (1.52 g, 94%). Mass Spec. 235.17 (MH+), Calc. for $C_{11}H_{14}N_4O_2$ 234.11.

Intermediate 31

(R)-Methyl 2-(4-(8-fluoro-2-oxo-1,2-dihydroquinazolin-3(4H)-yl)piperidine-1-carboxamido)-3-(7-methyl-1H-benzo[d][1, 2, 3]triazol-5-yl)propanoate. After the mixture of free amino ester (325 mg, 1.2 mmol), N,N-disuccinimidyl carbonate (DSC) (307 mg, 1.2 mmol ) and $^iPr_2NEt$ (0.84 mL, 4.8 mmol) in DMF (5 mL) was stirred at room temperature for 30 min, 8-fluoro-f3-(piperidin-4-yl)-3,4-dihydroquinazolin-2(1H)-one.HOAc (371 mg, 1.2 mmol) was added at once. The mixture was stirred at r.t. overnight, all volatiles were removed and the residue was subjected to flash chromatography (SiO2) using $CH_2Cl_2$/MeOH (100:1, 50:1, 25:1) as eluent to afford the title compound as an off-white solid (448 mg, 73%). $^1$HNMR ($CD_3OD$, 500 MHz) δ 7.52 (v br s, 1H), 7.19 (br s, 1H), 7.03-6.93 (m, 3H), 6.81 (d, J=8.2 Hz, 1H), 4.65-4.62 (m, 1H), 4.42-4.37 (m, 1H), 4.12-4.08 (m, 2H), 3.75 (s, 3H), 3.64-3.60 (m, 1H), 3.17-3.12 (m, 1H), 2.90-2.78 (m, 2H), 2.71 (br s, 3H), 1.63-1.59 (m, 4H); (MH+), Mass Spec. 510.37, Calc. for $C_{25}H_{28}FN_7O_4$ 509.22.

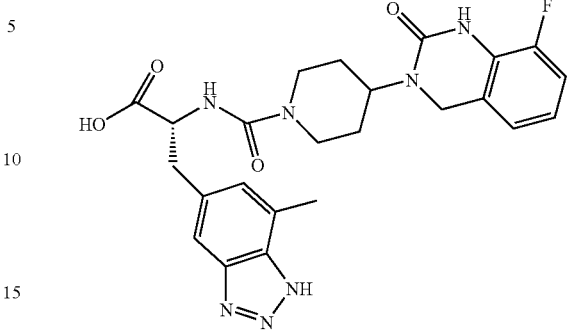

Intermediate 32

(R)-Methyl 2-(4-(8-fluoro-2-oxo-1,2-dihydroquinazolin-3(4H)-yl)piperidine-1-carboxamido)-3-(7-methyl-1H-benzo[d][1,2, 3]triazol-5-yl)propanoic acid. To the solution of the methyl ester (427 mg, 0.84 mmol) in MeOH (5 mL) and THF (5 mL), 2N solution of LiOH (2.1 mL, 4.2 mmol) was added dropwise at 0° C. and the mixture was stirred at this temperature for 6 h. All volatiles were removed under high vacuum and the residue was redissolved in 8 mL of water and acidified with 6N HCl to pH 1-2 at 0° C. The resulting white suspension was stirred at 0° C. for 30 min and sat at 0° C. for 2 h. After filtration, the wet solid was dried under high vacuum to yield the title compound as a white solid (345.3 mg, 83%). $^1$HNMR ($CD_3OD$, 300 MHz) δ 7.54 (s, 1H), 7.21 (s, 1H), 7.00-6.91 (m, 3H), 4.64-4.58 (m, 1H), 4.38-4.33 (m, 1H), 4.12-4.04 (m, 2H), 3.42-3.36 (m, 1H), 3.17-3.08 (m, 1H), 2.87-2.77 (m, 2H), 2.68 (s, 3H), 1.66-1.54 (m, 4H); Mass Spec. 496.56 (MH+), Calc. for $C_{24}H_{26}FN_7O_4$ 495.20.

Example 1

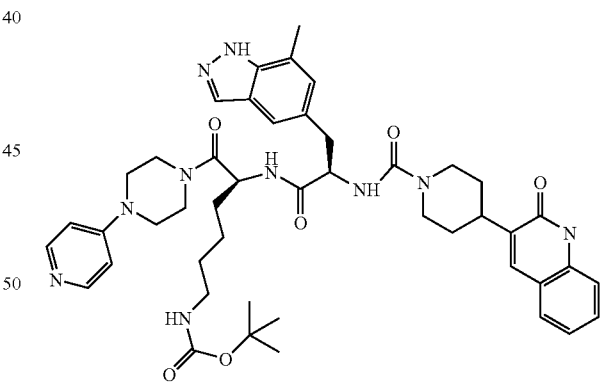

tert-Butyl (S)-5-((R)-3-(7-methyl-1H-indazol-5-yl)-2-(4-(2-oxo-1,2-dihydroquinolin-3-yl)piperidine-1-carboxamido)propanamido)-6-oxo-6-(4-(pyridin-4-yl)piperazin-1-yl)hexylcarbamate. To a solution of (R)-methyl 3-(7-methyl-1H-indazol-5-yl)-2-(4-(2-oxo-1,2-dihydroquinolin-3-yl)piperidine-1-carboxamido)propanoate (95 mg, 0.2 mmol) in DMF (2.0 mL) was added (S)-tert-butyl 5-amino-6-oxo-6-(4-(pyridin-4-yl)piperazin-1-yl)hexylcarbamate (78 mg, 0.2 mmol) followed by 2-(1H-benzotriazole-1-yl)-1,1,3,3-tetramethyluronium tetrafluoroborate (71 mg, 0.22 mmol) and triethylamine (1 mL). After stirring at room temperature for 2 h, the solvent was removed and the crude product was purified by flash chromatography using 7% methanol in dichloromethane containing 2% ammonium hydroxide (ammonia content 28-30%) to give tert-butyl (S)-5-((R)-3-(7-methyl-1H-indazol-5-yl)-2-(4-(2-oxo-1,2-dihydroquinolin-3-yl)piperidine-1-carboxamido)propanamido)-6-oxo-6-(4-(pyridin-4-yl)piperazin-1-yl)hexylcarbamate in 87% yield as white solid. $^1$H-NMR (CD$_3$OD) δ 8.11-8.10 (m, 2H), 7.97 (s, 1H), 7.61 (d, J=7.5 Hz, 1H), 7.50-7.44 (m, 3H), 7.32-7.30 (d, J=7.5 Hz, 2H), 7.23-7.20 (m, 1H), 7.13 (s, 1H), 6.77 (d, J=6.5 Hz, 1H), 4.83-4.81 (m, 1H), 4.67-4.65 (m, 1H), 4.14-4.08 (m, 2H), 3.82-3.78 (m, 2H), 3.69-3.62 (m, 1H), 3.60-3.53 (m, 1H), 3.48-2.80 (m, 10H), 2.52 (s, 3H), 1.84-1.78 (m, 2H), 1.69-1.61 (m, 1H), 1.40 (s, 9H), 1.49-1.11 (m, 8H); MS (ESI) 847 (M+H) ; R$_f$=2.34.

Example 2

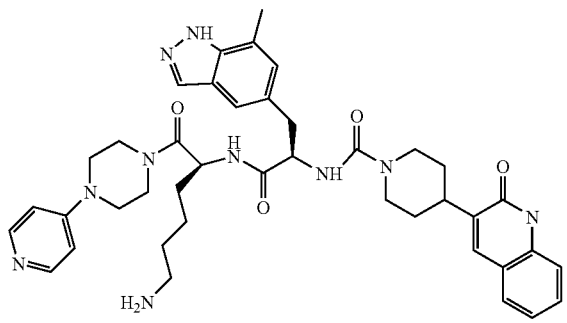

N-((R)-1-((S)-6-amino-1-oxo-1-(4-(pyridin-4-yl)piperazin-1-yl)hexan-2-ylamino)-3-(7-methyl-1H-indazol-5-yl)-1-oxopropan-2-yl)-4-(2-oxo-1,2-dihydroquinolin-3-yl)piperidine-1-carboxamide. To a suspension of tert-butyl (S)-5-((R)-3-(7-methyl-1H-indazol-5-yl)-2-(4-(2-oxo-1,2-dihydroquinolin-3-yl)piperidine-1-carboxamido)propanamido)-6-oxo-6-(4-(pyridin-4-yl)piperazin-1-yl)hexylcarbamate (230 mg, 0.27 mmol) in dichloromethane (10 mL) was added trifluoroacetic acid (10 mL) at 0° C. After 1 h at room temperature, the solvent was removed under high vacuum and then dissolved in methanol. The free base of title compound was liberated by passing the methanolic solution over Strata-X—C-33μ cation polymeric sorbent followed by elution with 3.0 M ammonia solution in methanol to give N-((R)-1-((S)-6-amino-1-oxo-1-(4-(pyridin-4-yl)piperazin-1-yl)hexan-2-ylamino)-3-(7-methyl-1H-indazol-5-yl)-1-oxopropan-2-yl)-4-(2-oxo-1,2-dihydroquinolin-3-yl)piperidine-1-carboxamide as a white solid in 72% yield. $^1$H-NMR (CD$_3$OD) δ 8.08-8.07 (m, J=2, 2H), 7.95 (s, 1H), 7.61 (d, J=10 Hz, 1H), 7.51-7.44 (m, 3H), 7.29 (d, J=10 Hz, 1H), 7.23-7.19 (m, 1H), 7.11 (s, 1H), 6.79-6.78 (m, 2H), 4.80-4.77 (m, 2H), 4.60-4.55 (m, 1H), 4.11-4.04 (m, 2H), 3.82-3.80 (m, 2H), 3.66-2.78 (m, 11H), 2.51 (s, 3H), 1.87-1.11 (m, 11H; MS (ESI) 747 (M+H); R$_f$=1.64.

Example 3

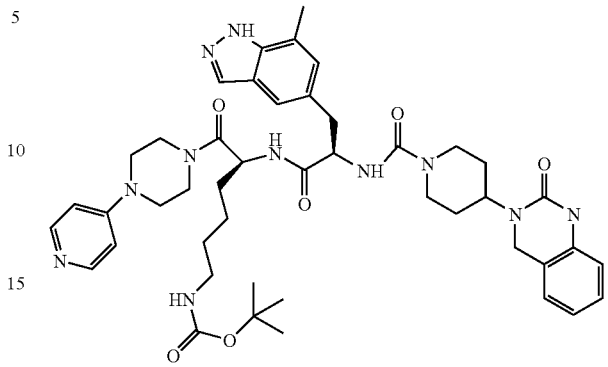

tert-Butyl (S)-5-((R)-3-(7-methyl-1H-indazol-5-yl)-2-(4-(2-oxo-1,2-dihydroquinazolin-3(4H)-yl)piperidine-1-carboxamido)propanamido)-6-oxo-6-(4-(pyridin-4-yl)piperazin-1-yl)hexylcarbamate. The title compound was prepared from (S)-tert-butyl 5-amino-6-oxo-6-(4-(pyridin-4-yl)piperazin-1-yl)hexylcarbamate and (R)-3-(7-methyl-1H-indazol-5-yl)-2-(4-(2-oxo-1,2-dihydroquinazolin-3 (4H)-yl)piperidine-1-carboxamido)propanoic acid using the same procedure as described for tert-butyl (S)-5-((R)-3-(7-methyl-1H-indazol-5-yl)-2-(4-(2-oxo-1,2-dihydroquinolin-3-yl)piperidine-1-carboxamido)propanamido)-6-oxo-6-(4-(pyridin-4-yl)piperazin-1-yl)hexylcarbamate. The title compound was obtained in 66% yield. MS (ESI) 850 (M+H) ; R$_f$=2.07.

Example 4

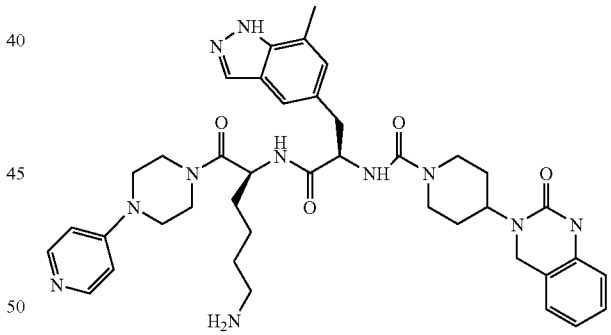

N-((R)-1-((S)-6-Amino-1-oxo-1-(4-(pyridin-4-yl)piperazin-1-yl)hexan-2-ylamino)-3-(7-methyl-1H-indazol-5-yl)-1-oxopropan-2-yl)-4-(2-oxo-1,2-dihydroquinazolin-3(4H)-yl)piperidine-1-carboxamide. The title compound was prepared from tert-Butyl (S)-5-((R)-3-(7-methyl-1H-indazol-5-yl)-2-(4-(2-oxo-1,2-dihydroquinazolin-3 (4H)-yl)piperidine-1-carboxamido)propanamido)-6-oxo-6-(4-(pyridin-4-yl)piperazin-1-yl)hexylcarbamate using the same procedure as described for N-((R)-1-((S)-6-amino-1-oxo-1-(4-(pyridin-4-yl)piperazin-1-yl)hexan-2-ylamino)-3-(7-methyl-1H-indazol-5-yl)-1-oxopropan-2-yl)-4-(2-oxo-1,2-dihydroquinolin-3-yl)piperidine-1-carboxamide. The title compound was obtained in 70% yield. MS (ESI) 750 (M+H) ; R$_f$=1.58.

Example 5

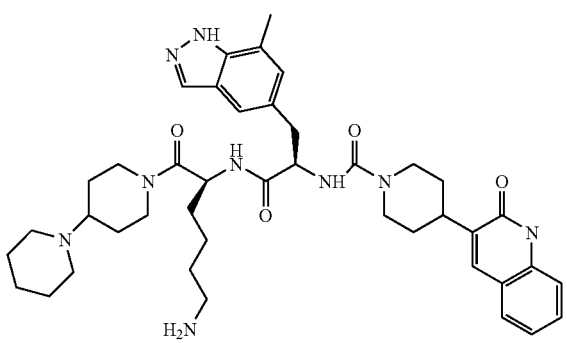

N-((R)-1-((S)-6-amino-1-oxo-1-(4-(piperidin-1-yl)piperidin-1-yl)hexan-2-ylamino)-3-(7-methyl-1H-indazol-5-yl)-1-oxopropan-2-yl)-4-(2-oxo-1,2-dihydroquinolin-3-yl)piperidine-1-carboxamide. To a solution of tert-Butyl (S)-5-((R)-2-amino-3-(7-methyl-1H-indazol-5-yl)propanamido)-6-oxo-6-(4-(piperidin-1-yl)piperidin-1-yl)hexylcarbamate (102 mg, 0.17 mmol) in DMF (3.0 mL) was added N,N'-disuccinimidyl carbonate (51 mg, 0.2 mmol) followed by triethylamine (1.0 mL). After 20 min stirring at room temperature, 3-(piperidin-4-yl)quinolin-2(1H)-one (45 mg, 0.2 mmol) was added and stirring continued for additional 12 h. The crude product was purified by using preparative HPLC starting from 30% solvent B (90% MeOH—10% $H_2O$—0.1% TFA)—70% solvent A (10% MeOH—90% $H_2O$—0.1% TFA) to 100% solvent B over a gradient time of 8 min and at a flow rate of 40 mL/min (column PHENOMENEX-LUNA 30×100 mm 10 μm C18). The solvent was evaporated from the desired pure fractions to give trifluoroacetic acid salt of N-((R)-1-((S)-6-amino-1-oxo-1-(4-(piperidin-1-yl)piperidin-1-yl)hexan-2-ylamino)-3-(7-methyl-1H-indazol-5-yl)-1-oxopropan-2-yl)-4-(2-oxo-1,2-dihydroquinolin-3-yl)piperidine-1-carboxamide as a white foam. The free base of title compound was liberated by passing the methanolic solution of trifluoroacetic acid salt over Strata-X-C-33μ cation polymeric sorbent followed by elution with 3.0 M ammonia solution in methanol. The desired compound was obtained as a white solid in 35% overall yield. $^1$H-NMR ($CD_3OD$) δ 8.02 (s, 1H), 7.68 (d, J=7 Hz, 1H), 7.58-7.46 (m, 3H), 7.36 (d, J=7 Hz, 1H), 7.29-7.23 (m, 1H), 7.11 (s, 1H), 4.95-4.4.78 (m, 2H), 4.65-4.56 (m, 2H), 4.17-4.07 (m, 2H), 3.31-2.62 (m, 18H), 2.55 (s, 3H), 2.07-1.13 (m, 22H); MS (ESI) 774 (M+Na); $R_f$=1.65.

Example 6

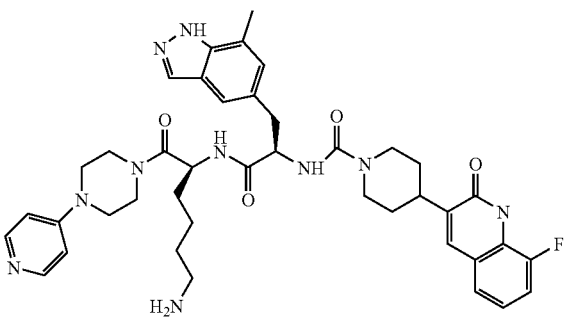

N-((R)-1-((S)-6-amino-1-oxo-1-(4-(pyridin-4-yl)piperazin-1-yl)hexan-2-ylamino)-3-(7-methyl-1H-indazol-5-yl)-1-oxopropan-2-yl)-4-(8-fluoro-2-oxo-1,2-dihydroquinolin-3-yl)piperidine-1-carboxamide. The title compound was prepared from tert-butyl (S)-5-((R)-2-amino-3-(7-methyl-1H-indazol-5-yl)propanamido)-6-oxo-6-(4-(pyridin-4-yl)piperazin-1-yl)hexylcarbamate and 8-fluoro-3-(piperidin-4-yl)quinolin-2(1H)-one using the same procedure as described for N-((R)-1-((S)-6-amino-1-oxo-1-(4-(piperidin-1-yl)piperidin-1-yl)hexan-2-ylamino)-3-(7-methyl-1H-indazol-5-yl)-1-oxopropan-2-yl)-4-(2-oxo-1,2-dihydroquinolin-3-yl)piperidine-1-carboxamide. The compound was isolated as a trifluoroacetic acid salt in 70% yield. MS (ESI) 765 (M+Na); $R_f$=1.68.

Example 7

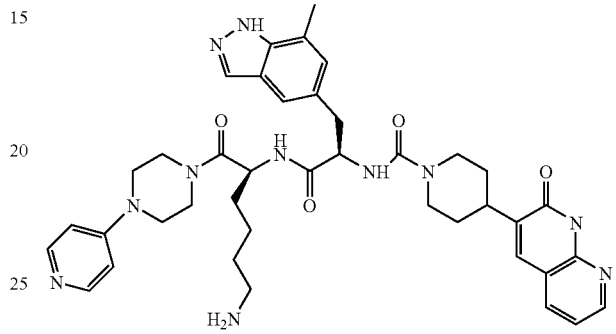

N-((R)-1-((S)-6-amino-1-oxo-1-(4-(pyridin-4-yl)piperazin-1-yl)hexan-2-ylamino)-3-(7-methyl-1H-indazol-5-yl)-1-oxopropan-2-yl)-4-(2-oxo-1,2-dihydro-1,8-naphthyridin-3-yl)piperidine-1-carboxamide. The title compound was prepared from tert-butyl (S)-5-((R)-2-amino-3-(7-methyl-1H-indazol-5-yl)propanamido)-6-oxo-6-(4-(pyridin-4-yl)piperazin-1-yl)hexylcarbamate and 3-(piperidin-4-yl)-1,8-naphthyridin-2(1H)-one using the same procedure as described for N-((R)-1-((S)-6-amino-1-oxo-1-(4-(piperidin-1-yl)piperidin-1-yl)hexan-2-ylamino)-3-(7-methyl-1H-indazol-5-yl)-1-oxopropan-2-yl)-4-(2-oxo-1,2-dihydroquinolin-3-yl)piperidine-1-carboxamide. The compound was isolated as a trifluoroacetic acid salt in 52% yield. MS (EST) 748 (M+Na); $R_f$=1.49.

Example 8

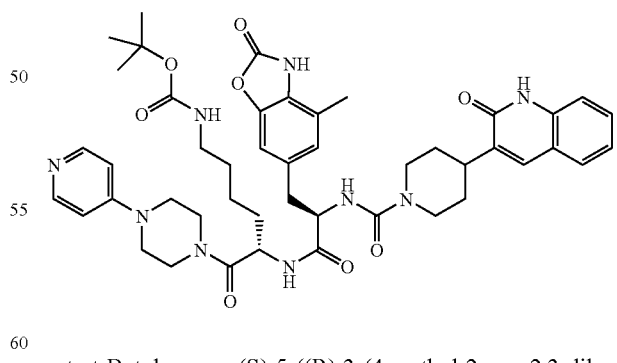

tert-Butyl (S)-5-((R)-3-(4-methyl-2-oxo-2,3-dihydrobenzo[d]oxazol-6-yl)-2-(4-(2-oxo-1,2-dihydroquinolin-3-yl)piperidine-1-carboxamido)propanamido)-6-oxo-6-(4-(pyridin-4-yl)piperazin-1-yl)hexylcarbamate. To a 20 mL of vial was added the acid (70 mg, 0.14 mmol, 1 equiv), lysine B (67.3 mg, 0.17 mmol, 1.2 equiv), DMF (5 mL), and i-$Pr_2$NEt (0.15 mL, 0.87 mmol, 6 equiv). The mixture was stirred to form a clear solution and TBTU (46 mg, 0.14 mmol, 1 equiv) was added. After it was stirred at r.t. for 20 h, all volatiles were removed and the residue was subjected to flash chromatography (SiO$_2$) using 2M NH$_3$-MeOH/CH$_2$Cl$_2$ (1:12) as eluent to afford an off-white solid. This off-white solid was subjected again to flash chromatography (SiO$_2$) using 2M NH$_3$-MeOH/CH$_2$Cl$_2$ (1:20 then 1:9) as eluent to afford the title compound as an off-white solid (89 mg, 74% yield). $^1$HNMR (CD$_3$OD, 500 MHz) δ 8.52 (d, J=6.4 Hz, 2H), 8.07-8.05 (m, 2H), 7.89 (t, J=8.2 Hz, 1H), 7.72 (d, J=8.2 Hz, 1H), 7.64 (t, J=7.6 Hz, 1H), 7.41 (s, 1H), 7.33 (s, 1H), 7.22 (d, J=6.7 Hz, 2H), 4.98-4.95 (m, 1H), 4.57-4.52 (m, 2H), 4.30-4.23 (m, 2H), 4.14-4.09 (m, 1H), 4.03-3.99 (m, 1H), 3.95-3.84 (m, 3H), 3.56-3.51 (m, 1H), 3.46-3.36 (m, 4H), 3.35-3.25 (m, 2H), 2.71 (s, 3H), 2.43 (s, 1H), 2.40-2.35 (m, 4H), 2.30-2.28 (m, 2H), 2.16-2.10 (m, 1H), 2.00-1.87 (m, 2H), 1.82 (s, 5H), 1.78 (s, 4H), 1.71-1.63 (m, 2H); Mass Spec. 864.33 (MH$^+$), Calc. for C$_{46}$H$_{57}$N$_9$O$_8$ 863.43; R$_f$: 2.30 min; LC/MS conditions: Start B %: 0; Final B %: 100; Gradient time: 3 min; Stop time: 4 min; Flow rate: 4 mL/min; Wavelength: 220 nm; Solvent A: 10% MeOH—90% H2O—0.1% TFA; Solvent B: 90 MeOH—10% H2O—0.1% TFA; Column: PHENOMENEX-LUNA 4.6×50 mm S10.

Example 9

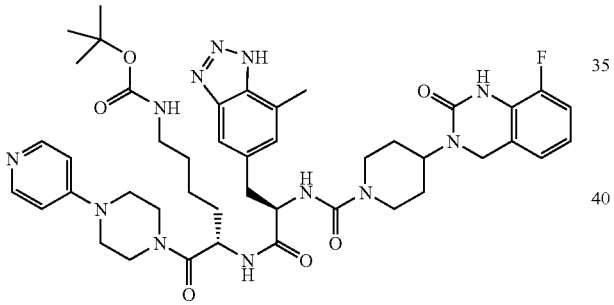

tert-Butyl (S)-5-((R)-2-(4-(8-fluoro-2-oxo-1,2-dihydroquinazolin-3(4H)-yl)piperidine-1-carboxamido)-3-(7-methyl-1H-benzo[d][1,2,3]triazol-5-yl)propanamido)-6-oxo-6-(4-(pyridin-4-yl)piperazin-1-yl)hexylcarbamate. $^1$HNMR (CD$_3$OD, 500 MHz) δ 8.57 (d, J=6.4 Hz, 2H), 7.99 (s, 1H), 7.63 (s, 1H), 7.45-7.34 (m, 3H), 7.28 (d, J=6.4 Hz, 2H), 5.08-5.05 (m, 1H), 4.82-4.75 (m, 1H), 4.54-4.47 (m, 2H), 4.31-4.27 (m, 2H), 4.16-4.13 (m, 1H), 4.07-4.03 (m, 1H), 3.99-3.87 (m, 6H), 3.55-3.50 (m, 1H), 3.42-3.36 (m, 2H), 3.31-3.25 (m, 1H), 3.22-3.17 (m, 1H), 3.12 (s, 3H), 2.61-2.59 (m, 0.5H), 2.45-2.37 (m, 3.5H), 2.15-2.08 (m, 1H), 2.06-1.91 (m, 4H), 1.84 (s, 5H), 1.80 (s, 4H), 1.68-1.60 (m, 4H); Mase Spec. 869.40 (MH$^+$), Calc. for C$_{44}$H$_{57}$FN$_{12}$O$_6$ 868.45; R$_f$: 1.49 min; LC/MS conditions: Start B %: 0; Final B %: 100; Gradient time: 3 min; Stop time: 4 min; Flow rate: 4 mL/min; Wavelength: 220 nm; Solvent A: 5% MeCN—95% H2O—10 mM NH4OAc; Solvent B: 95 MeCN—5% H2O—10 mM NH4OAc; Column: Xterrra MS c18 5 µm 4.6×50 mm.

We claim:
1. A compound according to Formula I

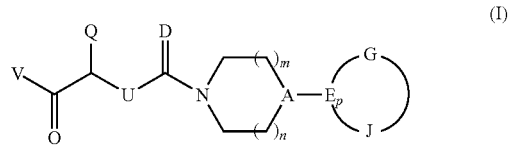

or a pharmaceutically acceptable salt thereof,
wherein:
V is (R$^1$)(R$^2$)NCOCH(R$^4$)NH where the carbon bearing R$^4$ has an absolute configuration of either R or S;
R$^4$ is C$_{1-6}$alkyl substituted in the ω-position with amino, formylamino, C$_{1-6}$alkylamino, C$_{1-6}$dialkylamino, C$_{1-6}$alkoxycarbonylamino, C$_{1-6}$alkanoylamino, or benzyloxycarbonylamino;
R$^1$ and R$^2$ together with the nitrogen to which they are attached form X,
wherein X is azetidinyl, pyrrolyl, pyrrolinyl, pyrrolidinyl, imidazolinyl, imidazolidinyl, pyrazolinyl, pyrazolidinyl, azepinyl, diazepinyl, piperazinyl, piperidinyl, morpholino or thiomorpholino;
wherein X is optionally substituted with Y, wherein Y is dioxolanyl, C$_{1-9}$alkyl, C$_{2-9}$alkenyl, C$_{2-9}$alkynyl, C$_{1-4}$alkylamino, C$_{1-4}$dialkylamino, C$_{1-4}$alkoxy, C$_{3-7}$cycloalkyl, phenyl, azetidinyl, furanyl, thienyl, pyrrolyl, pyrrolinyl, pyrrolidinyl, pyrrolidinonyl, imidazolyl, imidazolinyl, imidazolidinyl, imidazolidinonyl, pyrazolyl, pyrazolinyl, pyrazolidinyl, azepinyl, diazepinyl, pyridyl, pyrimidinyl, dihydrobenzimidazolonyl, piperazinyl, piperidinyl, morpholino, benzothiazolyl, benzisothiazolyl or thiomorpholino;
and wherein X and Y are optionally interrupted with Z, wherein Z is NHC(O)O, NHC(O)NH, NC(O)NH$_2$, NH, C$_{1-3}$alkylene, C$_{1-3}$alkylene, C$_{1-3}$alkenylene-NHC(O)O—C$_{1-3}$alkylene; and optionally and independently substituted with 1 or 2 of the same or different substituents selected from the group consisting of C$_{1-4}$alkyl, amino, C$_{1-3}$alkylamino, [(C$_{1-3}$alkyl)$_2$amino]C$_{1-6}$alkyl, (C$_{1-3}$alkyl)$_{0-2}$ureido, phenyl and benzyl;
X and Y optionally and independently contain 1 or 2 carbonyls wherein the carbon atom of said carbonyl is a member of the heterocycles comprising X and Y;
Q is Q' or Q";
wherein
Q' is (S$^y$)$_s$R$^3$; and
Q" is NH(S$^y$)$_s$R$^3$, NHC(O)(S$^y$)$_s$R3, NHC(O)O(S$^y$)$_s$R$^3$, NHC(O)NH(S$^y$)$_s$R$^3$, O(S$^y$)$_s$R$^3$, (S$^y$)$_s$NHR$^3$, (S$^y$)$_s$NHC(O)R$^3$, (S$^y$)$_s$NHC(O)OR$^3$, (S$^y$)$_s$NHC(O)NHR$^3$ or (S$^y$)$_s$OR$^3$; wherein S$^y$ is C$_{1-3}$alkylene or C$_{1-3}$alkylidene and s is 0 or 1;
U is CH$_2$, O, or NH, provided that if Q is Q", then U is CH$_2$;
R$^3$ is indazolyl, benzotriazolyl, benzooxazolinonyl;
and wherein R$^3$ is optionally substituted with 1 to 3 of the same or different substituents selected from the group consisting of benzyl, phenyl, phenoxy, (C$_{1-4}$)phenylalkoxy, (C$_{1-3}$)benzoylalkyl, cyano, amino, nitro, halo, C$_{1-6}$alkyl, (C$_{1-3}$)haloalkyl, (C$_{1-3}$)haloalkoxy, (C$_{1-3}$)alkylamine, (C$_{1-3}$)dialkylamine, OR$^{3'}$, C(O)R$^{3'}$, C(O)OR$^{3'}$, OC(O)R$^{3'}$, N(R$^{3'}$)$_2$, C(O)N(R$^{3'}$)$_2$, N(R$^{3'}$)C (O)(R$^{3'}$)$_2$, N(R$^{3'}$)C(O)N(R$^{3'}$)$_2$, N(R$^{3'}$)C(O)OR$^{3'}$, OC(O)N(R$^{3'}$)$_2$, N(R$^{3'}$)SO$_2$R$^{3'}$, SO$_2$N(R$^{3'}$)$_2$ and SO$_2$R$^{3'}$;

R$^{3'}$ is H or C$_{1-6}$alkyl, provided that if R$^{3a}$ is C(O)R$^{3'}$, CHC(O)OR$^{3'}$, CH(CH$_3$)C(O)OR$^{3'}$ or C(O)OR$^{3'}$, then said C(O)R$^{3'}$, CHC(O)OR$^{3'}$, CH(CH$_3$)C(O)OR$^{3'}$ or C(O)OR$^{3'}$ are unsubstituted;

D is O;

A is CH;

m and n are independently 1;

E is N, CH or C;

p is 1;

G, J and E together form A$^x$ where

A$^x$ is a fused heterocycle having two fused rings with 5 to 7 members in each of said rings, said heterocycle containing one to four of the same or different heteroatoms selected from the group consisting of O, N and S and optionally containing 1 or 2 carbonyls wherein the carbon atom of said carbonyl is a member of said fused heterocycle;

wherein A$^x$ is optionally substituted with C$_{1-4}$alkyl, C$_{1-4}$alkoxy, C$_{1-4}$haloalkyl, cyano, C$_{3-7}$cycloalkyl, phenyl, halophenyl, halo, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl or morpholine.

2. A compound of claim 1 where the carbon bearing R$^4$ is of the (S) configuration.

3. A compound of claim 1 where X is piperazinyl or piperidinyl and Y is pyridinyl or piperidinyl.

4. A compound of claim 1 where R$^4$ is C$_{1-6}$alkyl substituted in the ω-position with amino, C$_{1-6}$alkylamino, C$_{1-6}$dialkylamino, C$_{1-6}$alkoxycarbonylamino, or C$_{1-6}$alkanoylamino.

5. A compound of claim 1 where R$^4$ is aminobutyl or (t-butoxycarbonylamino)butyl.

6. A compound of claim 1 where Q is (S$^y$)$_n$R$^3$.

7. A compound of claim 1 where Q is (indazolyl)methyl, (benzotriazolyl)methyl, or (benzoxazolinonyl)methyl optionally substituted with 1 to 3 of the same or different substituents selected from the group consisting of halo, cyano, or C$_{1-2}$alkyl, or C$_{1-2}$halolkyl.

8. A compound of claim 1 where U is NH.

9. A composition comprising a compound of claim 1 and a pharmaceutically acceptable carrier.

10. A method of treating migraine in a patient in need thereof comprising the administration of an antimigraine effective amount of a compound of claim 1.

* * * * *

UNITED STATES PATENT AND TRADEMARK OFFICE
CERTIFICATE OF CORRECTION

PATENT NO. : 7,834,007 B2  Page 1 of 1
APPLICATION NO. : 11/508568
DATED : November 16, 2010
INVENTOR(S) : Xiaojun Han et al.

It is certified that error appears in the above-identified patent and that said Letters Patent is hereby corrected as shown below:

Claim 1:

Column 38, line 60, after "benzotriazolyl,", insert -- or --.

Column 40, line 3, change "morpholine" to -- morpholino --.

Claim 6:

Column 40, line 13, change "$(S^y)_n R^3$" to -- $(S^y)_s R^3$ --.

Signed and Sealed this
Sixth Day of December, 2011

David J. Kappos
*Director of the United States Patent and Trademark Office*